US008628914B2

(12) United States Patent
Allen et al.

(10) Patent No.: US 8,628,914 B2
(45) Date of Patent: Jan. 14, 2014

(54) QUANTITATIVE HELICASE ASSAY

(75) Inventors: Nadia Allen, Montgomery Village, MD (US); Peter Qiu, Gaithersburg, MD (US)

(73) Assignee: QIAGEN Gaithersburg, Inc., Gaithersburg, MD (US)

(*) Notice: Subject to any disclaimer, the term of this patent is extended or adjusted under 35 U.S.C. 154(b) by 12 days.

(21) Appl. No.: 13/116,810

(22) Filed: May 26, 2011

(65) Prior Publication Data
US 2011/0318731 A1    Dec. 29, 2011

Related U.S. Application Data

(60) Provisional application No. 61/348,397, filed on May 26, 2010.

(51) Int. Cl.
*C12Q 1/00* (2006.01)
*C12Q 1/68* (2006.01)
*C07H 21/00* (2006.01)
*C07H 21/02* (2006.01)
*C07H 21/04* (2006.01)

(52) U.S. Cl.
USPC .............. 435/4; 435/6.1; 536/22.1; 536/23.1; 536/24.3

(58) Field of Classification Search
USPC ...................... 435/4, 6.1; 536/22.1
See application file for complete search history.

(56) References Cited

U.S. PATENT DOCUMENTS

| | | | | |
|---|---|---|---|---|
| 3,687,808 | A | 8/1972 | Merigan | 195/28 |
| 4,845,205 | A | 7/1989 | Dinh | 536/28 |
| 5,130,302 | A | 7/1992 | Spielvogel | 514/45 |
| 5,134,066 | A | 7/1992 | Rogers | 435/91 |
| 5,175,273 | A | 12/1992 | Bischofberger | 536/27 |
| 5,210,015 | A * | 5/1993 | Gelfand et al. | 435/6.11 |
| 5,367,066 | A | 11/1994 | Urdea | 536/24.3 |
| 5,432,272 | A | 7/1995 | Benner | 536/25.3 |
| 5,457,187 | A | 10/1995 | Gmeiner | 536/25.5 |
| 5,459,255 | A | 10/1995 | Cook | 536/27.13 |
| 5,484,908 | A | 1/1996 | Froehler | 536/24.31 |
| 5,502,177 | A | 3/1996 | Matteucci | 536/26.6 |
| 5,525,711 | A | 6/1996 | Hawkins | 536/22.1 |
| 5,552,540 | A | 9/1996 | Haralambidis | 536/25.34 |
| 5,563,037 | A | 10/1996 | Sutherland | 435/6 |
| 5,587,469 | A | 12/1996 | Cook | 536/23.1 |
| 5,594,121 | A | 1/1997 | Froehler | 536/23.5 |
| 5,596,091 | A | 1/1997 | Switzer | 536/24.5 |
| 5,614,617 | A | 3/1997 | Cook | 514/44 |
| 5,681,941 | A | 10/1997 | Cook | 536/23.1 |
| 5,705,344 | A * | 1/1998 | Giordano et al. | 435/6.18 |
| 6,291,669 | B1 | 9/2001 | Kwiatkowski | 536/25.3 |
| 6,294,664 | B1 | 9/2001 | Ravikumar | 536/25.3 |
| 6,379,897 | B1 * | 4/2002 | Weidenhammer et al. | 435/6.11 |
| 6,773,885 | B1 * | 8/2004 | Walder et al. | 435/6.1 |
| 7,282,328 | B2 | 10/2007 | Kong | 435/6 |
| 7,445,900 | B2 | 11/2008 | Gelfan | 435/6 |
| 2002/0127549 | A1 * | 9/2002 | Zhang et al. | 435/6 |
| 2009/0298187 | A1 | 12/2009 | Nazarenko | 436/6 |

FOREIGN PATENT DOCUMENTS

| | | |
|---|---|---|
| EP | 0 070 685 | 1/1983 |
| JP | 2008 099619 | 5/2008 |
| WO | WO 97/17076 | 5/1997 |
| WO | WO 97/17471 | 5/1997 |
| WO | WO 00/06710 | 2/2000 |
| WO | WO00/06710 * | 2/2000 |
| WO | WO 01/25487 | 4/2001 |

OTHER PUBLICATIONS

An et al. Charactyerization of a thermostable UvrD helicase and its participation in helicase dependent amplification. J. of Biological Chemistry 280(32) : 28952 (2005).*
Marras et al., Multiplex detection of single-nucleotide variations using molecular beacons. Genetic Analysis: Biomolecular Egineering 14 : 151 (1999).*
Matthews et al. Analytical Biochemistry 169 :1 (1988).*
The Stratagene Catalog p. 39 (1988).*
Vincent et al., Helicase-dependent isothermal DNA amplification. EMBO reports 5(8) : 795 (2004).*
Zhang et al, Development of a novel helicase assay using electrochemiluminescence. Analytical Biochemistry 293 : 31 (2001).*
International Search Report issued on Jul. 29, 2011 for PCT/US2011/038167 filed on May 26, 2011, which claims priority to U.S. Appl. No. 61/348,397 (Applicant—Qiagen Gaithersburg, Inc.; Inventors—Allen et al.).
Written Opinion issued on Jul. 29, 2011 for PCT/US2011/038167 filed on May 26, 2011 which claims priority to U.S. Appl. No. 61/348,397 (Applicant—Qiagen Gaithersburg, Inc.; Inventors—Allen et al.).
Ausubel FM, Brent R, Kingston RE, Moore DD, Seidman JG, Smith JA, Struhl K. (Eds). (1987) John Wiley & Sons, New York. Current Protocols in Molecular Biology. vol. 1, Unit 1.6—Minipreps of Plasmid DNA and Unit 1.7—CsCl/Ethidium Bromide Preparations of Plasmid DNA, Unit 2.2—Preparation of Genomic DNA from Mammalian Tissue.
Beaucage SL, Caruthers MH. (1981) Deoxynucleoside phosphoramidites—a new class of key intermediates for deoxypolynucleotide synthesis. Tetrahedron Lett. 22(20): 1859-1862.
Belon CA, Frick DN. (2008) Monitoring helicase activity with molecular beacons. Biotechniques. 45(4): 433-440, 442.
Caruthers JM, McKay DB. (2002) Helicase structure and mechanism. Curr Opin Struct Biol. 12(1):123-133.
Collins R, McCarthy TV. (2003) Purification and characterization of *Thermus thermophilus* UvrD. Extremophiles. 7(1):35-41.
Dong F, Weitzel SE, von Hippel PH. (1996) A coupled complex of T4 DNA replication helicase (gp41) and polymerase (gp43) can perform rapid and processive DNA strand-displacement synthesis. Proc Natl Acad Sci USA. 93(25): 14456-14461.

(Continued)

*Primary Examiner* — Ethan C Whisenant
(74) *Attorney, Agent, or Firm* — Ballard Spahr LLP

(57) ABSTRACT

Disclosed herein are methods and kits relating to detection and quantitation of helicase activity.

17 Claims, 12 Drawing Sheets

(56) References Cited

OTHER PUBLICATIONS

Englisch U, Gauss DH. (1991) Chemically modified oligonucleotides as probes and inhibitors. Angewandte Chemie, Intl Ed. 30(6): 613-722.
Gorbalenya AE, Koonin EV. (1993) Helicases: amino acid sequence comparisons and structure-function relationships. Curr Opin Struct Biol. 3(3): 419-429.
Grainge I, Scaife S, Wigley DB. (2003) Biochemical analysis of components of the pre-replication complex of *Archaeoglobus fulgidus*. Nucleic Acids Res. 31(16): 4888-4898.
Guo Z, Guilfoyle RA, Thiel AJ, Wang R, Smith LM. (1994) Direct fluorescence analysis of genetic polymorphisms by hybridization with oligonucleotide arrays on glass supports. Nucleic Acids Res. 22(24): 5456-5465.
Hall JG, Eis PS, Law SM, Reynaldo LP, Prudent JR, Marshall DJ, Allawi HT, Mast AL, Dahlberg JE, Kwiatkowski RW, de Arruda M, Neri BP, Lyamichev VI. (2000) Sensitive detection of DNA polymorphisms by the serial invasive signal amplification reaction. Proc Natl Acad Sci USA. 97(15): 8272-8277.
Hall RH, Todd A, Webb RF. (1957) Nucleotide. Part XLI. Mixed anhydrides an intermediate in the synthesis of dinucleoside phosphates. J Chem Soc. 3291-3296.
Harmon FG, Kowalczykowski SC. (2001) Biochemical characterization of the DNA helicase activity of the *Escherichia coli* RecQ helicase. J Biol Chem. 276(1): 232-243.
Henegariu O, Bray-Ward P, Ward DC. (2000) Custom fluorescent-nucleotide synthesis as an alternative method for nucleic acid labeling. Nat Biotechnol. 18(3): 345-348.
Hermanson et al. (1992) Immobmilized Affinity Ligand Techniques. Academic Press, Inc., San Diego, California, Contents, pp. vii-xv.
Hicham Alaoui-Ismaili M, Gervais C, Brunette S, Gouin G, Hamel M, Rando RF Bedard J. (2000) A novel high throughput screening assay for HCV NS3 helicase activity. Antiviral Res. 46(3): 181-193.
Holland PM, Abramson RD, Watson R, Gelfand DH. (1991) Detection of specific polymerase chain reaction product by utilizing the 5'-3' exonuclease activity of *Thermus aquaticus* DNA polymerase. Proc Natl Acad Sci USA. 88(16): 7276-7280.
Hoy CA, Carswell C, Schimke RT. (1993) Bromodeoxyuridine/DNA analysis of replication in CHO cells after exposure to UV light. Mutat Res. 290(2): 217-230.
Itakura K, Rossi JJ, Wallace RB. (1984) Synthesis and use of synthetic oligonucleotides. Annu Rev Biochem. 53: 323-356.
Iyer RP, Egan W, Regan JB, Beaucage SL. (1990) 3-H-1,2-benzodithiole-3-one 1, 1-dioxide as an improved sulfurizing reagent in the solid-phase synthesis of oligodeoxyribonucleosdie phosphorothioates. J Am Chem Soc. 112: 1253-1254.
Johnstone et al. (1987) Immunochemistry in Practice. Blackwell Scientific Publications, Oxford, England, pp. 209-216 and 241-242.
Kaplan DL, Steitz TA. (1999) DnaB from *Thermus aquaticus* unwinds forked duplex DNA with an asymmetric tail length dependence. J Biol Chem. 274(11): 6889-6897.
Karlin S, Altschul SF. (1990) Methods for assessing the statistical significance of molecular sequence features by using general scoring schemes. Proc Natl Acad Sci U S A. 87(6): 2264-2268.
Karlin S, Altschul SF. (1993) Applications and statistics for multiple high-scoring segments in molecular sequences. Proc Natl Acad Sci USA. 90(12): 5873-5877.
Kerkhof L. (1992) A comparison of substrates for quantifying the signal from a nonradiolabeled DNA probe. Anal Biochem. 205(2): 359-364.
Khrapko KR, Khorlin AA, Ivanov IB, Chernov BK, Lysov IuP, Vasilenko SK, Florent'ev VL, Mirzabekov AD. (1991) Hybridization of DNA with oligonucleotides immobilized in a gel: a convenient method for recording single base substituions. Mol Biol (Mosk). 25(3): 718-730.
Kyono K, Miyashiro M, Taguchi I. (1998) Detection of hepatitis C virus helicase activity using the scintillation proximity assay system. Anal Biochem. 257(2): 120-126.
Langer PR, Waldrop AA, Ward DC. (1981) Enzymatic synthesis of biotin-labeled polynucleotides: novel nucleic acid affinity probes. Proc Natl Acad Sci USA. 78(11): 6633-6637.

Lesnik EA, Freier SM. (1995) Relative thermodynamic stability of DNA, RNA, and DNA:RNA hybrid duplexes: relationship with base composition and structure. Biochemistry. 34(34): 10807-10815.
Letsinger RL, Lunsford WB. (1976) Synthesis of thymidine oligonucleotides by phosphite triester intermediates. J Am Chem Soc. 98(12): 3655-3661.
Matteucci MD, Caruthers MH. (1981) Synthesis of deoxyoligonucleotides on a polymer support. J Am Chem Soc. 103:3185-3191.
Mechanic LE, Frankel BA, Matson SW. (2000) *Escherichia coli* MutL loads DNA helicase II onto DNA. J Biol Chem. 275(49): 38337-38346.
Miyoshi D, Nakao A, Sugimoto N. (2002) Molecular crowding regulates the structural switch of the DNA G-quadruplex. Biochemistry. 41(50): 15017-15024.
Narang SA, Brousseau R, Hsiung HM, Michniewicz JJ. (1980) Chemical synthesis of deoxyoligonucleotides by the modified triester method. Methods Enzymol. 65(1): 610-620.
Nielsen PE, Egholm M, Buchardt O. (1994) Peptide nucleic acid (PNA). A DNA mimic with a peptide backbone. Bioconjug Chem. 5(1): 3-7.
Pease AC, Solas D, Sullivan EJ, Cronin MT, Holmes CP, Fodor SP. (1994) Light-generated oligonucleotide arrays for rapid DNA sequence analysis. Proc Natl Acad Sci USA. 91(11): 5022-5026.
Pless RC, Letsinger RL. (1975) Solid support synthesis of oligothymidylates using phosphorochloridates and 1-alkylimidazoles. Nucleic Acids Res. 2(6): 773-786.
Rouillard JM, Zuker M, Gulari E. (2003) OligoArray 2.0: design of oligonucleotide probes for DNA microarrays using a thermodynamic approach. Nucleic Acids Res. 31(12): 3057-3062.
Rychlik W, Spencer WJ, Rhoads RE. (1990) Optimization of the annealing temperature for DNA amplification in vitro. Nucleic Acids Res. 18(21): 6409-6412.
Sambrook et al. (1989) Molecular Cloning: A Laboratory Manual. 2nd Ed., Cold Spring Harbor Laboratory Press, Cold Spring Harbor, N.Y. Chapters 5, 6.
Sanghvi YS. (1993) Heterocyclic base modifications in nucleic acids and their applications in antisense oligonucleotides. Antisense Research and Applications. (Crooke et al, eds., CRC Press) Chapters 15-16, pp. 273-301.
Sano H, Imokawa M, Sager R. (1988) Detection of heavy methylation in human repetitive DNA subsets by a monoclonal antibody against 5-methylcytosine. Biochim Biophys Acta. 951(1): 157-165.
Schweitzer B, Kingsmore S. (2001) Combining nucleic acid amplification and detection. Curr Opin Biotechnol. 12(1): 21-27.
Solinas A, Brown LJ, McKeen C, Mellor JM, Nicol J, Thelwell N, Brown T. (2001) Duplex Scorpion primers in SNP analysis and FRET applications. Nucleic Acids Res. 29(20): E96.
Soultanas P, Wigley DB. (2001) Unwinding the 'Gordian knot' of helicase action. Trends Biochem Sci. 26(1): 47-54.
Stimpson DI, Hoijer JV, Hsieh WT, Jou C, Gordon J, Theriault T, Gamble R, Baldeschwieler JD. (1995) Real-time detection of DNA hybridization and melting on oligonucleotide arrays by using optical wave guides. Proc Natl Acad Sci USA. 92(14): 6379-6383.
Thelwell N, Millington S, Solinas A, Booth J, Brown T. (2000) Mode of action and application of Scorpion primers to mutation detection. Nucleic Acids Res. 28(19): 3752-3761.
Tyagi S, Kramer FR. (1996) Molecular beacons: probes that fluoresce upon hybridization. Nat Biotechnol. 14(3): 303-308.
Wansink DG, Schul W, van der Kraan I, van Steensel B, van Driel R, de Jong L. (1993) Fluorescent labeling of nascent RNA reveals transcription by RNA polymerase II in domains scattered throughout the nucleus. J Cell Biol. 122(2): 283-293.
Whitcombe D, Theaker J, Guy SP, Brown T, Little S. (1999) Detection of PCR products using self-probing amplicons and fluorescence. Nat Biotechnol. 17(8): 804-807.
Yamaguchi M, Dao V, Modrich P. (1998) MutS and MutL activate DNA helicase II in a mismatch-dependent manner. J Biol Chem. 273(15): 9197-9201.
Yu H, Chao J, Patek D, Mujumdar R, Mujumdar S, Waggoner AS. (1994) Cyanine dye dUTP analogs for enzymatic labeling of DNA probes. Nucleic Acids Res. 22(15): 3226-3232.

\* cited by examiner

FIGURE 9
A
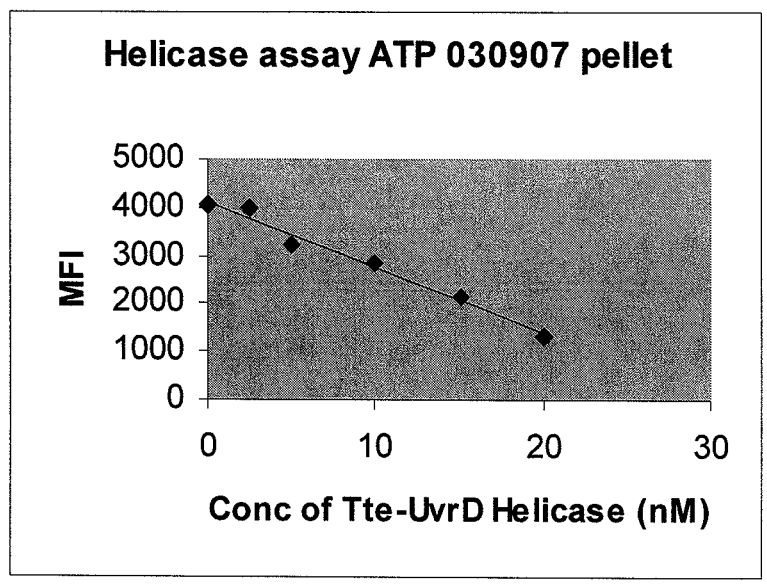
B
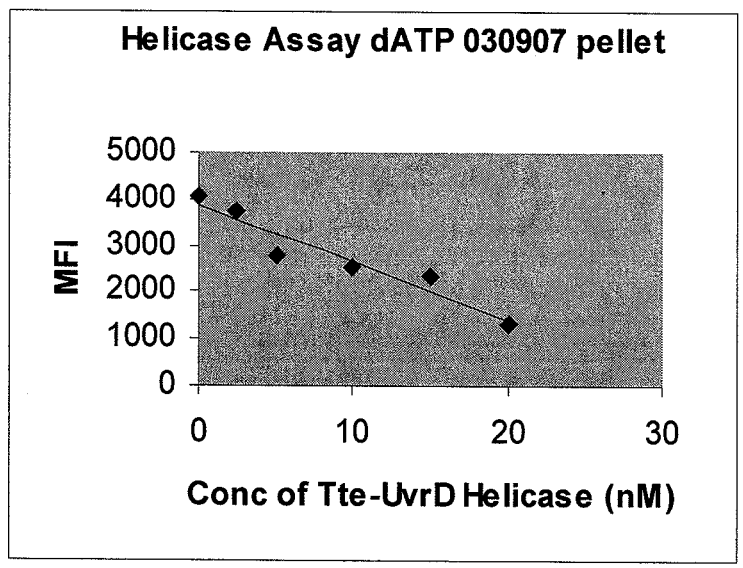

FIGURE 10
A
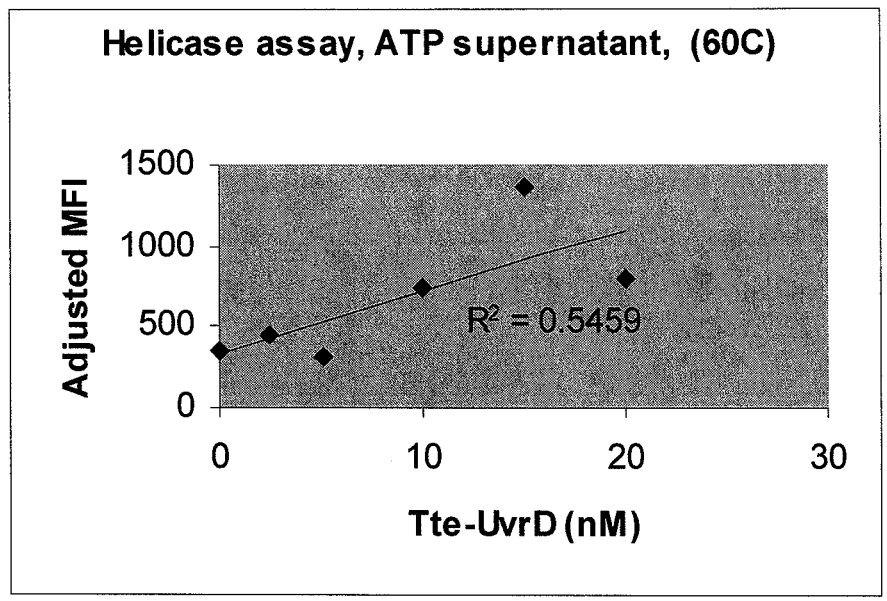
B
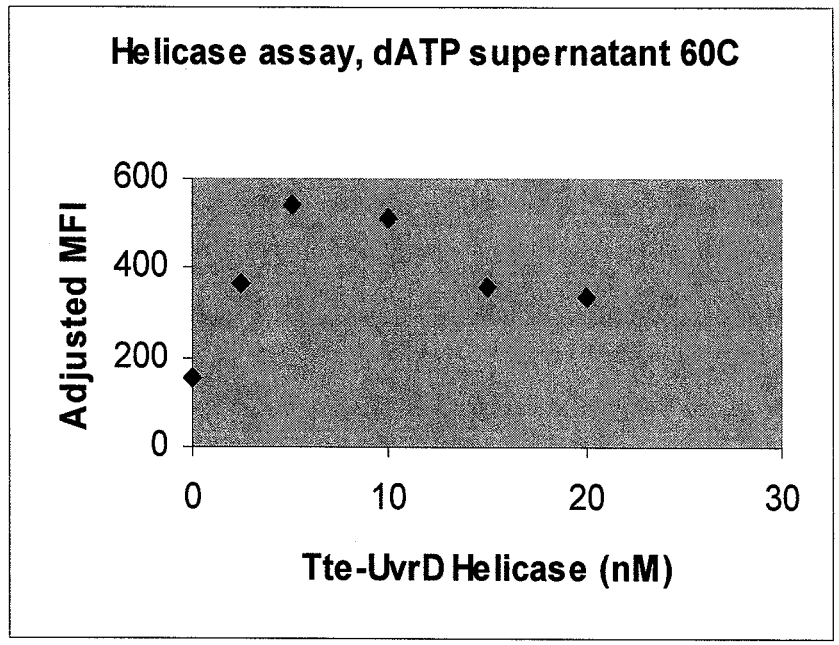

FIGURE 11
A
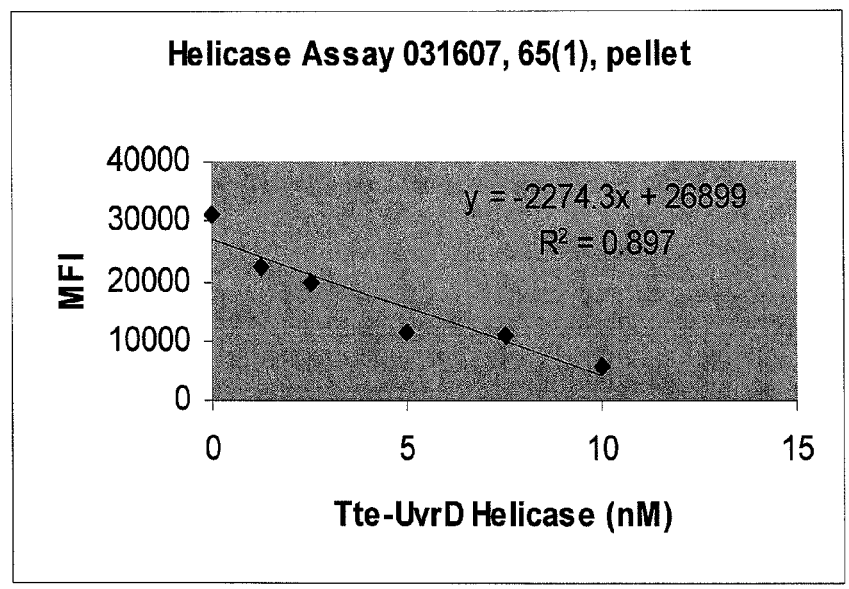
B
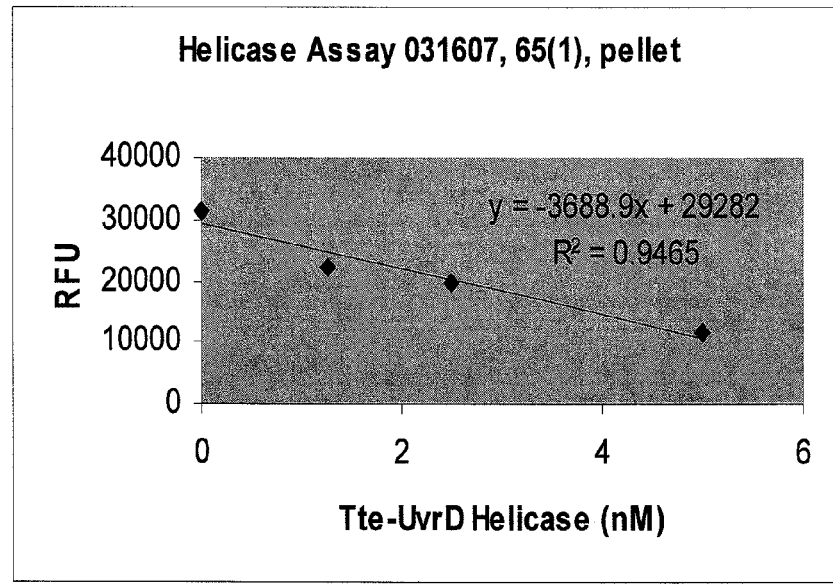

```
                        SEQUENCE LISTING

<160> NUMBER OF SEQ ID NOS: 3

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 1
aattgtttcc aaatgcactg gccgtcgttt tac                                 33

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 2
gtaaaacgac ggccagtgca tttggaaaca att                                 33

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 3
gtaaaacgac ggccagtgca tttggaaaca att                                 33
```

QUANTITATIVE HELICASE ASSAY

CROSS-REFERENCE TO RELATED PATENT APPLICATIONS

This application claims priority to U.S. Provisional Application No. 61/348,397, filed on May 26, 2010, which is hereby incorporated herein by reference in their entirety.

BACKGROUND OF THE INVENTION

Helicases are a class of enzymes that are motor proteins that move directionally along a nucleic acid phosphodiester backbone, separating two annealed nucleic acid strands (i.e. DNA, RNA, or RNA-DNA hybrid) using energy derived from ATP hydrolysis. Many cellular processes (DNA replication, transcription, translation, recombination, DNA repair, ribosome biogenesis) involve the separation of nucleic acid strands. Helicases are often utilized to separate strands of a DNA double helix or a self-annealed RNA molecule using the energy from ATP hydrolysis, a process characterized by the breaking of hydrogen bonds between annealed nucleotide bases. They move incrementally along one nucleic acid strand of the duplex with a directionality and processivity specific to each particular enzyme. There are many helicases (14 confirmed in *E. coli*, 24 in human cells) resulting from the great variety of processes in which strand separation must be catalyzed.

Studies have shown that helicases do not merely wait passively for the fork to widen, but play an active role in forcing the fork to open, thus it is an active motor unwinding its substrate.

The current technologies available that attempt to examine helicase activity include: 1) ATPase activity assays, which are quantitative but do not provide a direct method of measuring unwinding activity; and 2) radioactive helicase assays, which are not quantitative but provide a direct measurement of unwinding (or helicase activity). However, both of these assays are very laborious. What is needed in the art are efficient, uniform methods and assays for determining helicase activity.

SUMMARY OF THE INVENTION

Disclosed herein are methods of measuring helicase activity comprising providing a nucleic acid duplex comprising a first immobilizable nucleic acid strand and a labeled second strand; immobilizing the nucleic acid duplex; contacting the immobilized nucleic acid substrate duplex with a helicase to form a helicase-duplex mixture; incubating the helicase-duplex mixture with a trap oligonucleotide under conditions for helicase activity; separating non-immobilized nucleic acids, and; detecting the label present with the immobilized nucleic acids, wherein a decrease in the amount of label present indicates helicase activity.

Also disclosed are methods for measuring helicase activity comprising: providing a nucleic acid duplex comprising a first immobilizable nucleic acid strand and a labeled second strand; immobilizing the nucleic acid duplex; contacting the immobilized nucleic acid substrate duplex with a helicase to form a helicase-duplex mixture; incubating the helicase-duplex mixture with a trap oligonucleotide under conditions for helicase activity; separating non-immobilized nucleic acids, and detecting the amount of label present with the non-immobilized nucleic acids, wherein the presence of label over background indicates helicase activity.

Further disclosed are methods of measuring helicase activity comprising: providing a nucleic acid duplex comprising a first immobilizable nucleic acid strand and a labeled second strand; contacting the immobilized nucleic acid substrate duplex with a helicase to form a helicase-duplex mixture; incubating the helicase-duplex mixture with a trap oligonucleotide under conditions for helicase activity; immobilizing the first immobilizable strand of the nucleic acid duplex, separating non-immobilized nucleic acids; and detecting the label present with the immobilized nucleic acids, wherein a decrease in the amount of label present indicates helicase activity.

Also disclosed are methods of measuring helicase activity comprising: providing a nucleic acid duplex comprising a first nucleic acid strand and a labeled second strand; contacting the nucleic acid substrate duplex of step a) with a helicase to form a helicase-duplex mixture; incubating the helicase-duplex mixture with an immobilizable trap oligonucleotide under conditions for helicase activity; immobilizing the immobilizable trap oligonucleotide; separating non-immobilized nucleic acids, and; detecting the label present with immobilized trap oligonucleotide, wherein an increase in the amount of label present indicates helicase activity.

Also disclosed are methods of measuring helicase activity comprising: providing a nucleic acid duplex comprising a first immobilizable nucleic acid strand and a labeled second strand; contacting the nucleic acid substrate duplex of step a) with a helicase to form a helicase-duplex mixture; incubating the helicase-duplex mixture with an immobilizable trap oligonucleotide under conditions for helicase activity; immobilizing the immobilizable trap oligonucleotide; separating the immobilized first immobilizable nucleic acid strand from the immobilizable trap oligonucleotide, and; detecting the label present with the immobilized trap oligonucleotide, wherein an increase in the amount of label present indicates helicase activity.

Also disclosed are methods of measuring helicase activity comprising: providing a nucleic acid duplex comprising a first immobilizable nucleic acid strand and a labeled second strand; contacting the nucleic acid substrate duplex of step a) with a helicase to form a helicase-duplex mixture; incubating the helicase-duplex mixture with an immobilizable trap oligonucleotide under conditions for helicase activity; immobilizing the immobilizable trap oligonucleotide and the first immobilizable nucleic acid strand; separating the immobilized first immobilizable nucleic acid strand from the immobilizable trap oligonucleotide, and; detecting the label present with the immobilized first immobilizable nucleic acid strand, wherein a decrease in the amount of label present indicates helicase activity.

Further disclosed are methods for measuring helicase activity comprising: providing a nucleic acid duplex comprising a first nucleic acid strand and a second nucleic acid strand; determining the amount of label present; contacting the nucleic acid duplex with a helicase to form a helicase-duplex mixture; incubating the helicase-duplex mixture with a trap oligonucleotide under conditions for helicase activity, wherein the trap oligonucleotide comprises a fluorescent change probe portion; and detecting the label present in the mixture, wherein an increase in the amount of label present indicates helicase activity.

Further disclosed are methods for measuring helicase activity comprising: providing a nucleic acid duplex comprising a first nucleic acid strand and a labeled second nucleic acid strand; determining the amount of label present; contacting the nucleic acid duplex with a helicase to form a helicase-duplex mixture; incubating the helicase-duplex mixture with a trap oligonucleotide comprising a label quencher under conditions for helicase activity; and detecting the label present with the immobilized nucleic acids, wherein a decrease in the amount of label present indicates helicase activity.

Further disclosed are methods for measuring helicase activity comprising: providing a nucleic acid duplex comprising a first nucleic acid strand and a second nucleic acid strand, wherein the second nucleic acid strand comprises a quencher; contacting the nucleic acid duplex with a helicase to form a helicase-duplex mixture; incubating the helicase-duplex mixture with a labeled trap oligonucleotide under conditions for helicase activity; and detecting the label present with the immobilized nucleic acids, wherein a decrease in the amount of label present indicates helicase activity.

Additional advantages of the disclosed methods and compositions will be set forth in part in the description which follows, and in part will be understood from the description, or can be learned by practice of the disclosed methods and compositions. The advantages of the disclosed methods and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

FIG. 9 shows side by side comparison of the helicase assay using ATP (graph A) vs. dATP (graph B). The results show minimal difference between the two compounds as measured by the fluorescence of the pellet, which represents bound material.

FIG. 10 shows side by side comparison of the helicase assay using ATP (graph A) vs. dATP (graph B). The results show minimal difference between the two compounds as measured by the fluorescence of the supernatant, which represents unbound material.

FIG. 11 depicts the plot showing all the data points from the helicase assay conducted with a range of helicase concentrations and in which dATP is added individually to each well of the plate. Graph B shows the first four data points of Graph A where the linear range is in tact.

DETAILED DESCRIPTION OF THE INVENTION

Figure 1:
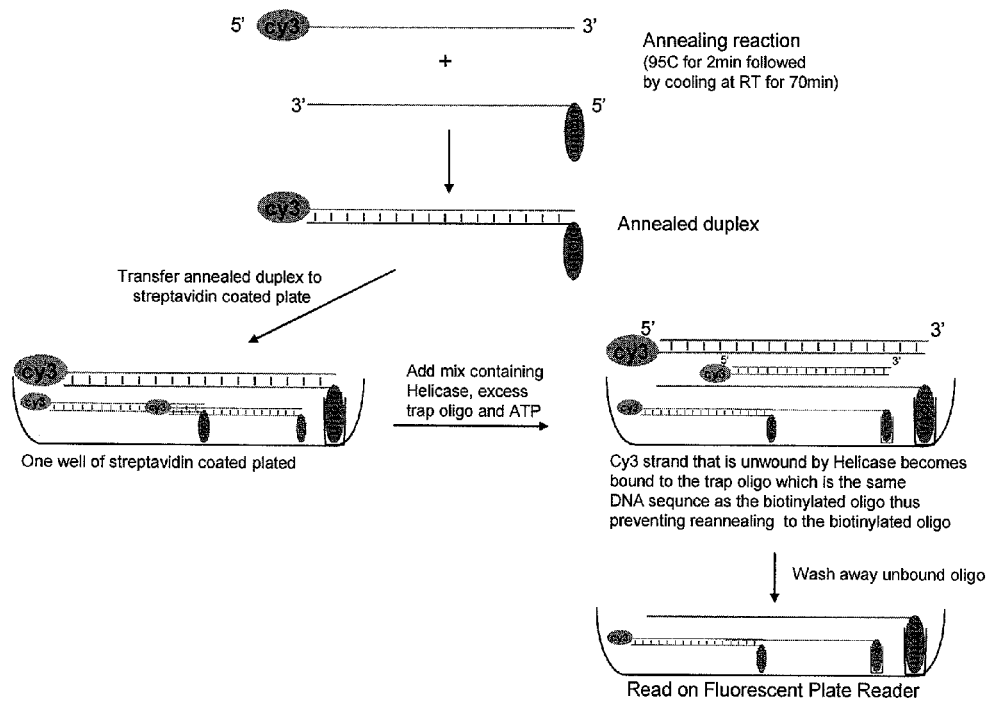
FIG. 1 provides a schematic representing one embodiment of the fluorescent based helicase assay of the present invention.
Figure 2:
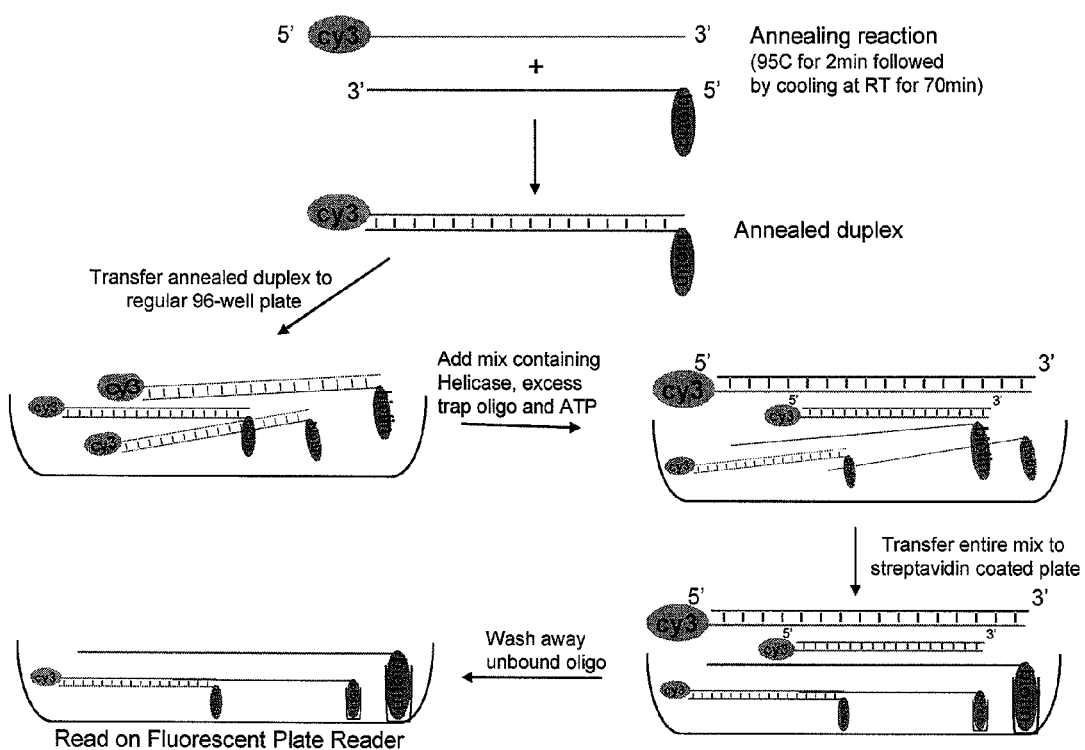
FIG. 2 provides a schematic presenting another embodiment of the fluorescent based helicase assay of the present invention.

The present invention comprises methods and systems directed at determining helicase activity. The disclosed method and compositions can be understood more readily by reference to the following detailed description of particular embodiments and the Example included therein and to the Figures and their previous and following description.

All patents, patent applications and publications cited herein, whether supra or infra, are hereby incorporated by reference in their entireties into this application in order to more fully describe the state of the art as known to those skilled therein as of the date of the invention described and claimed herein. It is to be understood that this invention is not limited to specific synthetic methods, or to specific recombinant biotechnology methods unless otherwise specified, or to particular reagents unless otherwise specified.

Disclosed herein are methods of directly measuring helicase activity. It is important to determine (as well as quantify) helicase activity because there are multiple methods and assays available for using helicase molecules. For example, one of skill in the art can use the disclosed methods, assays, and compositions to determine which helicase is best to use with a given assay, whether a given helicase is working optimally, as well as which reaction conditions are best for a given helicase.

For example, the methods disclosed herein can be used in conjunction with "Helicase Dependent Amplification" (HDA) to determine which helicase to use, what the optimal conditions are for a given helicase, and what optimal reaction conditions are. Helicase-Dependent Amplification (HDA) is based on the unwinding activity of a DNA helicase. HDA uses a helicase rather than heat to separate the two strands of a DNA duplex generating single-stranded templates for the purpose of in vitro amplification of a target nucleic acid. Sequence-specific primers hybridize to the templates and are then extended by DNA polymerases to amplify the target sequence. This process repeats itself so that exponential amplification can be achieved at a single temperature.

Definitions and Nomenclature

The terminology used herein is for the purpose of describing particular embodiments only and is not intended to be limiting.

As used in the specification and the appended claims, the singular forms "a," "an" and "the" can include plural referents unless the context clearly dictates otherwise. Thus, for example, reference to "a preparation" includes mixtures of compounds, and the like. Reference to "a component" can include a single or multiple components or a mixture of components unless the context clearly dictates otherwise.

Ranges may be expressed herein as from "about" one particular value, and/or to "about" another particular value. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The word "or" as used herein means any one member of a particular list and also includes any combination of members of that list.

By "sample" is meant an animal; a tissue or organ from an animal; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components.

The term "nucleic acid" refers to double stranded or single stranded DNA, RNA molecules or DNA/RNA hybrids. The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof. Those nucleic acids which are double stranded nucleic acid molecules may be nicked or intact. The double stranded or single stranded nucleic acid molecules may be linear or circular. The duplexes may be blunt ended or have single stranded tails. The single stranded molecules may have secondary structure in the form of hairpins or loops and stems. The nucleic acid may be isolated from a variety of sources including the environment, food, agriculture, fermentations, biological fluids such as blood, milk, cerebrospinal fluid, sputum, saliva, stool, lung aspirates, swabs of mucosal tissues or tissue samples or cells. Nucleic acid samples may obtained from cells or viruses and may include any of: chromosomal DNA, extra chromosomal DNA including plasmid DNA, recombinant DNA, DNA fragments, messenger RNA, transfer RNA, ribosomal RNA, double stranded RNA or other RNAs that occur in cells or viruses. Any of the above described nucleic acids may be subject to modification where individual nucleotides within the nucleic acid are chemically altered (for example, by methylation). Modifications may arise naturally or by in vitro synthesis.

The term "target nucleic acid" refers to a nucleic acid sought to be amplified, detected, or otherwise identified. For example, a "target nucleic acid" can refer to a nucleic acid strand of a nucleic acid duplex that is complementary to a trap oligonucleotide. In some aspects the target nucleic acid is *Chlamydia trachomatis* ("CT") or *Neisseria gonorrhea* ("NG") DNA or RNA.

The term "duplex" or "hybrid" refers to a nucleic acid molecule that is double stranded in whole or part. For example, a "double-stranded probe-target hybrid" refers to a nucleic acid molecule formed when an oligonucleotide probe hybridizes with a denatured target nucleic acid to form a double stranded nucleic acid molecule in the area whereby the oligonucleotide probe is specifically hybridized to the denatured target nucleic acid. A "nucleic acid duplex" refers to a nucleic acid molecule formed when two complementary nucleic acid strands hybridize together to form a double stranded nucleic acid molecule in the region of complementarity. For example, a "nucleic acid duplex" can comprise a first immobilizable nucleic acid strand and a labeled second nucleic acid strand. The stability of a resulting hybrid or duplex can depend upon the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art.

The terms "melting," "unwinding" or "denaturing" refer to separating all or part of two complementary strands of a nucleic acid duplex or nucleic acid hybrid.

The terms "hybridization" or "hybridizes" is meant that the composition recognizes and physically interacts with another composition. For example, "hybridization" can refer to binding of an oligonucleotide primer to a region of a single-stranded nucleic acid template.

By "specifically binds" or "specifically hybridizes" is meant that the composition recognizes and physically interacts with its cognate target. For example, a primer can specifically bind to its target nucleic acid. For example, a primer specific to a sequence present in a cryptic plasmid can specifically hybridize to the cryptic plasmid and does not significantly recognize and interact with other targets or target nucleic acid sequences. The specificity of hybridization may be influenced by the length of the oligonucleotide primer, the temperature in which the hybridization reaction is performed, the ionic strength, and the pH.

By "probe," "primer," or "oligonucleotide" is meant a single-stranded DNA or RNA molecule of defined sequence that can base-pair to a second DNA or RNA molecule that contains a complementary sequence (the "target"). The term "primer" refers also to a single stranded nucleic acid capable of binding to a single stranded region on a target nucleic acid to facilitate polymerase dependent replication of the target nucleic acid. The stability of the resulting hybrid depends upon the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes or primers specific for target nucleic acids (for example, genes and/or mRNAs) have at least 80%-90% sequence complementarity, at least 91%-95% sequence complementarity, at least 96%-99% sequence complementarity, or at least 100% sequence complementarity to the region of the target to which they hybridize. Probes, primers, and oligonucleotides may be detectably-labeled, either radioactively, or non-radioactively, by methods well-known to those skilled in the art. Probes or oligonucleotide probes can be used for methods involving nucleic acid hybridization, such as: the described methods of forming double-stranded probe-target hybrids between an oligonucleotide probe and a denatured target nucleic acid. Primers and oligonucleotide primers can be used for methods involving nucleic acid hybridization, such as: synthesizing an extension product of an oligonucleotide primer hybridized to a target nucleic acid, which is complementary to the target nucleic acid or for amplifying a target nucleic acid in a tHDA reaction. Probes, primers and oligonucleotides can also be used for nucleic acid sequencing, reverse transcription and/or nucleic acid amplification by the polymerase chain reaction, single stranded conformational polymorphism (SSCP) analysis, restriction fragment polymorphism (RFLP) analysis, Southern hybridization, Northern hybridization, in situ hybridization, and electrophoretic mobility shift assay (EMSA).

By "primer set" is meant to mean at least two primers that each contain a complementary sequence to an opposite strand of the same target sequence. In a primer set, at least one of the two primers must be a "forward primer" at least one of the two primers must be a "reverse primer". A "forward primer" is a primer that is complementary to a sense strand of a target nucleic acid, wherein a "reverse primer" is a primer that is complementary to the complement of the sense strand of the target nucleic acid (also referred to as the anti-sense strand of the target nucleic acid). A primer set can be a pair of primers capable of being used in a tHDA reaction.

Similarly, by "oligonucleotide probe" is meant to mean a single-stranded DNA or RNA molecule of defined sequence that can base-pair to a second DNA or RNA molecule that contains a complementary sequence. For example, a trap oligonucleotide can be an oligonucleotide probe. In accordance with the methods described herein, one or more oligonucleotide probes can be contacted with a denatured nucleic acid sequence under conditions sufficient for the one or more polynucleotide probes to hybridize to a denatured nucleic acid duplex to form double-stranded probe-target hybrids. For example, a trap oligonucleotide can be contacted with a denatured nucleic acid duplex under conditions sufficient for the one or more trap oligonucleotides to hybridize to the denatured nucleic acid duplex to form double-stranded trap oligo-target hybrids. In some aspects, the target nucleic acid is DNA and the oligonucleotide probes are RNA.

By "amplicon" is meant to mean pieces of DNA formed as the products of natural or artificial amplification events. For example, they can be formed via the methods described herein, tHDA, polymerase chain reactions (PCR) or ligase chain reactions (LCR), as well as by natural gene duplication.

By "specifically hybridizes" is meant that a probe, primer, or oligonucleotide recognizes and physically interacts (that is, base-pairs) with a substantially complementary nucleic acid (for example, a target nucleic acid) under high stringency conditions, and does not substantially base pair with other nucleic acids.

By "high stringency conditions" is meant conditions that allow hybridization comparable with that resulting from the use of a DNA probe of at least 40 nucleotides in length, in a buffer containing 0.5 M NaHPO4, pH 7.2, 7% SDS, 1 mM EDTA, and 1% BSA (Fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. Other conditions for high stringency hybridization, such as for PCR, Northern, Southern, or in situ hybridization, DNA sequencing, etc., are well-known by those skilled in the art of molecular biology. (See, for example, F. Ausubel et al., Current Protocols in Molecular Biology, John Wiley & Sons, New York, N.Y., 1998).

The term "accessory protein," refers to any protein capable of stimulating helicase activity. For example, E. coli MutL protein is an accessory protein (Yamaguchi et al. J. Biol. Chem. 273:9197 9201 (1998); Mechanic et al., J. Biol. Chem. 275:38337 38346 (2000)) for enhancing UvrD helicase melting activity. In embodiments of the method, accessory proteins can be used with selected helicases. In alternative embodiments, unwinding of nucleic acids may be achieved by helicases in the absence of accessory proteins.

In certain embodiments a "cofactor" may be used. A "cofactor" refers to small-molecule agents that are required for the helicase unwinding activity. Helicase cofactors include nucleoside triphosphate (NTP) and deoxynucleoside triphosphate (dNTP) and magnesium (or other divalent cations). For example, ATP (adenosine triphosphate) may be used as a cofactor for UvrD helicase at a concentration in the range of 0.1 100 mM and preferably in the range of 1 to 10 mM (for example 3 mM). Similarly, dTTP (deoxythymidine triphosphate) may be used as a cofactor for T7 Gp4B helicase in the range of 1 10 mM (for example 3 mM).

The term "HDA" refers to Helicase Dependent Amplification which is an in vitro method for amplifying nucleic acids by using a helicase preparation for unwinding a double stranded nucleic acid to generate templates for primer hybridization and subsequent primer-extension. This process utilizes two oligonucleotide primers, each hybridizing to the 3'-end of either the sense strand containing the target sequence or the anti-sense strand containing the reverse-complementary target sequence. The HDA reaction is a general method for helicase-dependent nucleic acid amplification.

"Thermophilic Helicase Dependent Amplification" or "tHDA" refers to an isothermal amplification technology that utilizes helicase to unwind double-stranded DNA, removing the need for thermocycling. tHDA is a true isothermal DNA amplification method and has a simple reaction scheme, similar to PCR. Basic tHDA is described in U.S. Pat. No. 7,282,328 (Kong et al.) and is hereby incorporated by reference in its entirety.

The term "isothermal amplification" refers to amplification which occurs at a single temperature. This does not include the single brief time period (less than 15 minutes) at the initiation of amplification which may be conducted at the same temperature as the amplification procedure or at a higher temperature.

The term "helicase preparation" refers to a mixture of reagents that when combined with a DNA polymerase, a nucleic acid template, four deoxynucleotide triphosphates, and oligonucleotide primers are capable of achieving isothermal, specific nucleic acid amplification in vitro.

The term "trap oligonucleotide" refers to a single-stranded DNA or RNA molecule of defined sequence that can base-pair to a second DNA or RNA molecule that contains a complementary sequence. In accordance with the methods described herein, one or more trap oligonucleotides can be contacted with a denatured nucleic acid sequence under conditions sufficient for the one or more trap oligonucleotides to hybridize to the denatured target nucleic acid form double-stranded trap oligonucleotide-target hybrids. In some aspects, the trap oligonucleotide is designed to be complementary to the second nucleic acid sequence of a nucleic acid duplex. In some aspects, the trap oligonucleotide is designed to have the same sequence as the first nucleic acid sequence of a nucleic acid duplex.

The term "helicase" refers here to any enzyme capable of unwinding a double stranded nucleic acid enzymatically. For example, helicases are enzymes that are found in all organisms and in all processes that involve nucleic acid such as replication, recombination, repair, transcription, translation and RNA splicing. (Kornberg and Baker, DNA Replication, W.H. Freeman and Company (2nd ed. (1992)), especially chapter 11). An example of a helicase that can be used with the methods and kits described herein is Tte-UvrD helicase. Further examples of helicases are given below.

The term "detection label" or "label" refers to any molecule that can be associated with a nucleic acid, directly or indirectly, and which results in a measurable, detectable signal, either directly or indirectly. Further examples of detection labels are given below.

Materials

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if an oligonucleotide probe is disclosed and discussed and a number of modifications that can be made to a number of molecules including the oligonucleotide probe are discussed, each and every combination and permutation of the oligonucleotide probe and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Trap Oligonucleotides

A "trap oligonucleotide" refers to a single-stranded DNA or RNA molecule of defined sequence that can base-pair to a second DNA or RNA molecule that contains a complementary sequence (such as a single strand from the nucleic acid duplex that was separated by helicase activity). In accordance with the present invention, one or more trap oligonucleotides can be contacted with a denatured nucleic acid under conditions sufficient for the one or more trap oligonucleotides to hybridize to the denatured target nucleic acid (e.g. a second nucleic acid strand of a nucleic acid duplex) to form double-stranded trap-target hybrids. In one aspect, the target nucleic acid is DNA and the trap oligonucleotide is RNA.

In some aspects, one or more trap oligonucleotides are used (i.e. more than one probe). In one aspect, the trap oligonucleotides can be present in excess as compared to the nucleic acid duplex or in excess of the first nucleic acid strand of the nucleic acid duplex or in excess of the second nucleic acid strand of the nucleic acid duplex. One or more trap oligonucleotides can be specific for one or more nucleic acids (e.g. a second nucleic acid strand of a nucleic acid duplex).

In some aspects a trap oligonucleotide mixture comprising multiple sets of oligonucleotides can be used to simultaneously hybridize to a mixture of desired target nucleic acids. Furthermore, multiple trap oligonucleotides can be used to hybridize to different regions of the same target sequence.

The trap oligonucleotides described herein allow for sensitive detection of one or more target nucleic acid sequence (e.g. a second nucleic acid strand of a nucleic acid duplex), while also achieving excellent specificity against even very similar related target nucleic acid sequences.

One method of determining the one or more trap oligonucleotides can be found in U.S. patent application Ser. No. 12/426,076, which is specifically incorporated by reference in its entirety and especially for its teaching of oligonucleotide probes and methods of using and identifying the same. For example, depending on the target nucleic acid of interest, and the corresponding non-target nucleic acids, the one or more trap oligonucleotides can be prepared to have lengths sufficient to provide target-specific hybridization to the sought after target nucleic acid sequence.

For example, the one or more trap oligonucleotides can each have a length of at least about 5, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000 nucleotides, or any value between.

The one or more trap oligonucleotides can each have a length of at least about 15 nucleotides, illustratively, about 15 to about 1000, about 20 to about 800, about 30 to about 400, about 40 to about 200, about 50 to about 100, about 20 to about 60, about 20 to about 40, about 20 to about 20 and about 25 to about 30 nucleotides. In some aspects, the one or more trap oligonucleotides each have a length of about 25 to about 50 nucleotides. In some aspects, the probes have a length of 25 nucleotides. In some aspects, all of the probes in a set will have the same length, such as 25 nucleotides, and will have very similar melting temperatures to allow hybridization of all of the probes in the set under the same hybridization conditions.

The one or more trap oligonucleotides can each have a length of at least about 5 nucleotides, illustratively, about 5 to about 50, about 5 to about 100, about 5 to about 150, about 5 to about 200, about 5 to about 250, about 5 to about 300, about 5 to about 350, about 5 to about 400, about 5 to about 450, about 5 to about 500, about 5 to about 550, about 5 to about 600, about 5 to about 650, about 5 to about 700, about 5 to about 750, about 5 to about 800, about 5 to about 850, about 5 to about 900, about 5 to about 950, or about 5 to about 1000. In some aspects, all of the probes in a set will have the same length, such as 5 nucleotides, and will have very similar melting temperatures to allow hybridization of all of the probes in the set under the same hybridization conditions.

The one or more trap oligonucleotides can each have a length of at least about 5 nucleotides, illustratively, about 15 to about 50, about 15 to about 100, about 15 to about 150, about 15 to about 200, about 15 to about 250, about 15 to about 300, about 15 to about 350, about 15 to about 400, about 15 to about 450, about 15 to about 500, about 15 to about 550, about 15 to about 600, about 15 to about 650, about 15 to about 700, about 15 to about 750, about 15 to about 800, about 15 to about 850, about 15 to about 900, about 15 to about 950, or about 15 to about 1000. In some aspects, all of the probes in a set will have the same length, such as 15 nucleotides, and will have very similar melting temperatures to allow hybridization of all of the probes in the set under the same hybridization conditions.

The one or more trap oligonucleotides can each have a length of at least about 5 nucleotides, illustratively, about 50 to about 50, about 50 to about 100, about 50 to about 150, about 50 to about 200, about 50 to about 250, about 50 to about 300, about 50 to about 350, about 50 to about 400, about 50 to about 450, about 50 to about 500, about 50 to about 550, about 50 to about 600, about 50 to about 650, about 50 to about 700, about 50 to about 750, about 50 to about 800, about 50 to about 850, about 50 to about 900, about 50 to about 950, or about 50 to about 1000. In some aspects, all of the probes in a set will have the same length, such as 50 nucleotides, and will have very similar melting temperatures to allow hybridization of all of the probes in the set under the same hybridization conditions.

Bioinformatics tools can also be employed to design the one or more trap oligonucleotides. For example, Oligoarray 2.0, a software program that designs specific oligonucleotides can be utilized. Oligoarray 2.0 is described by Rouillard et al. Nucleic Acids Research, 31: 3057-3062 (2003), which is incorporated herein by reference. Oligoarray 2.0 is a program which combines the functionality of BLAST (Basic Local Alignment Search Tool) and Mfold (Genetics Computer Group, Madison, Wis.). BLAST, which implements the statistical matching theory by Karlin and Altschul (Proc. Natl. Acad. Sci. USA 87:2264 (1990); Proc. Natl. Acad. Sci. USA 90:5873 (1993), is a widely used program for rapidly detecting nucleotide sequences that match a given query sequence One of ordinary skill in the art can provide a database of sequences, which are to be checked against, for example presence or absence of CT or NG. The target sequence of interest, e.g. the outer membrane protein gene for CT, can then be BLASTed against that database to search for any regions of identity. Melting temperature (Tm) and % GC can then be computed for one or more polynucleotide probes of a specified length and compared to the parameters, after which secondary structure also can be examined. Once all parameters of interest are satisfied, cross hybridization can be checked with the Mfold package, using the similarity determined by BLAST. The various programs can be adapted to determine the one or more polynucleotide probes meeting the desired specificity requirements. For example, the parameters of the program can be set to prepare polynucleotides of 25 nt length, Tm range of 55-95° C., a GC range of 35-65%, and no secondary structure or cross-hybridization at 55° C. or below.

Trap oligonucleotides can also be immobilizable. For example, disclosed herein are immobilizable trap oligonucleotides. Immobilizable trap oligonucleotides can be immobilized as described elsewhere herein where methods and compositions regarding immobilization of nucleic acids and oligonucleotides are described.

Trap oligonucleotides can also be labeled. Suitable labels are described elsewhere herein where detection labels are described. For example, disclosed herein are trap oligonucleotides that comprise one or more detection labels.

Also disclosed herein are trap oligonucleotides that comprise a fluorescent change molecule or a fluorescent change probe portion. A "fluorescent change probe portion" of a nucleic acid strand (e.g. a trap oligonucleotide) is a part of or can comprise the entire length of the nucleic acid strand, so long as the fluorescent change probe portion does not interfere with the ability of the nucleic acid strand to hybridize to its complement. For example, disclosed herein are trap oligonucleotides that comprise molecular beacons, Amplifluors, FRET probes, cleavable FRET probes, TaqMan probes, scorpion primers, fluorescent triplex oligos including but not limited to triplex molecular beacons or triplex FRET probes, fluorescent water-soluble conjugated polymers, PNA probes, and QPNA probes. DxS' Scorpion Primers as described in U.S. Pat. No. 7,445,900; Whitcombe, et al, 1999, Nature Biotech 17, 804-807; Thelwell, et al. (2000), Nucleic Acid Research 29, 3752-3761; Solinas, et al. (2001), Nucleic Acid Research 29, 1-9. The disclosed trap oligonucleotides that comprise a fluorescent change probe portion can be used to hybridize to a target nucleic acid strand (e.g. a second nucleic acid strand of a nucleic acid duplex) such that when the trap oligonucleotide hybridizes to the target nucleic acid strand, the detection label present in the fluorescent change probe portion becomes activated, and thereby generates a detectable signal. Examples of fluorescent change probes and primer are described elsewhere herein.

Also disclosed herein are trap oligonucleotides that comprise a detectable label or a quencher. For example, the trap oligonucleotides can comprise a detectable label that can be quenched by a quencher present on a complementary nucleic acid strand. A trap oligonucleotide can also comprise a quencher that is capable of quenching a detectable label present on a complementary nucleic acid strand.

B. Nucleic Acid Duplex/Target Nucleic Acid Duplex

A "nucleic acid duplex" or a "target nucleic acid duplex" refers to a double stranded nucleic acid, comprising, in part a first nucleic acid strand and a second nucleic acid strand. For example, a "target nucleic acid duplex" can refer to a double stranded nucleic acid, comprising, in part a target nucleic acid sequence (e.g. second nucleic acid strand) and a complement of a target nucleic acid sequence (e.g. first nucleic acid strand). A target nucleic acid duplex can be created by synthesizing an extension product of an oligonucleotide primer which is complementary to the target nucleic acid to which the oligonucleotide primer is hybridized, by means of a DNA polymerase.

In some aspects, the target nucleic acid duplex is separated by helicase activity. When this occurs, two separate nucleic acid strands are provided.

In some aspects, one of the two strands of a nucleic acid duplex can be immobilized, while the other is not. In some aspects, neither strand is immobilized.

In some aspects, one of the two strands of a nucleic acid duplex can be labeled with a detectable label, while the other is not. In some aspects, neither strand is labeled.

In some aspects, one of the two strands of a nucleic acid duplex can be hybridized to a quencher, while the other is not. In some aspects, neither strand is hybridized to a quencher.

One of skill in the art will recognize the various ways in which the target nucleic acid duplex can be separated, labeled, immobilized, and separated.

C. Helicase Preparations

In the methods described herein, the helicase can be provided in a "helicase preparation." A "helicase preparation" must at least comprise a helicase. A "helicase preparation" may also comprise one or more other compositions that enhance helicase activity, including, but not limited to an energy source as a nucleotide triphosphate (NTP) or deoxynucleotide triphosphate (dNTP), a single strand DNA binding protein (SSB), salt, reagents to modify pH, other chemical reagents, such as denaturation reagents including urea and dimethyl-sulfoxide (DMSO), and other cofactors.

For example, a helicase preparation can include a helicase, an energy source such as a nucleotide triphosphate (NTP) or deoxynucleotide triphosphate (dNTP), and a single strand DNA binding protein (SSB). One or more additional reagents may also be included in the helicase preparation, where these are selected from the following: one or more additional helicases, an accessory protein, small molecules, chemical reagents and a buffer. Where a thermostable helicase is utilized in a helicase preparation, the presence of a single stranded binding protein is optional. Examples of various helicases that can be used with the methods and assays disclosed herein are given below.

Single-Stranded DNA Binding Proteins

Some helicases show improved activity in the presence of single-strand binding proteins (SSB). In these circumstances, the choice of SSB is generally not limited to a specific protein. Examples of single strand binding proteins are T4 gene 32 protein, *E. coli* SSB, T7 gp2.5 SSB, phage phi29 SSB (Romberg and Baker, supra (1992)) and truncated forms of the aforementioned. SSBs can be used with the methods and assays disclosed herein, but are not required.

Other Chemical Reagents

In addition to salt and pH, other chemical reagents, such as denaturation reagents including urea and dimethyl-sulfoxide (DMSO) can be added to partially denature or de-stabilize the duplex DNA. Again, while these components can be added to the methods and assays disclosed herein, they are not required. These other chemical reagents can also be part of the helicase preparation. Denaturation can be compared in different concentrations of denaturation reagents with or without SSB protein. In this way, chemical compounds can be identified which increase helicase efficiency and/or substitute for SSB in single-strand (ss) DNA stabilization. Most of the biomacromolecules such as nucleic acids and proteins are designed to function and/or form their native structures in a living cell at much high concentrations than in vitro experimental conditions. Polyethylene glycol (PEG) has been used to create an artificial molecular crowding condition by excluding water and creating electrostatic interaction with solute polycations (Miyoshi, et al., Biochemistry 41:15017 15024 (2002)). When PEG (7.5%) is added to a DNA ligation reaction, the reaction time is reduced to 5 min (Quick Ligation Kit, New England Biolabs, Inc. (Beverly, Mass.)). PEG has also been added into helicase unwinding assays to increase the efficiency of the reaction (Dong, et al., Proc. Natl. Acad. Sci. USA 93:14456 14461 (1996)). PEG or other molecular crowding reagents may increase the effective concentrations of enzymes and nucleic acids and thus reduce the reaction time and amount of protein concentration needed for the reaction.

Cofactors

ATP or TTP is a common energy source for highly processive helicases. On average one ATP molecule is consumed by a DNA helicases to unwind 1 to 4 base pairs (Kornberg and Baker, supra (1992)). In some aspects of the described methods, a UvrD-based helicase system had an optimal initial ATP concentration of 3 mM. To amplify a longer target, more ATP may be consumed as compared to a shorter target. In these circumstances, it may be desirable to include a pyruvate kinase-based ATP regenerating system for use with the helicase (Harmon and Kowalczykowski, Journal of Biological Chemistry 276:232 243 (2001)).

Helicases

The term "helicase" refers here to any enzyme capable of unwinding a double stranded nucleic acid enzymatically. For example, helicases are enzymes that are found in all organisms and in all processes that involve nucleic acid such as replication, recombination, repair, transcription, translation and RNA splicing. (Kornberg and Baker, DNA Replication, W.H. Freeman and Company (2nd ed. (1992)), especially chapter 11). Any helicase that translocates along DNA or RNA in a 5' to 3' direction or in the opposite 3' to 5' direction may be used in present embodiments of the invention. This includes helicases obtained from prokaryotes, viruses, archaea, and eukaryotes or recombinant forms of naturally occurring enzymes as well as analogues or derivatives having the specified activity. Examples of naturally occurring DNA helicases, described by Kornberg and Baker in chapter 11 of their book, DNA Replication, W.H. Freeman and Company (2nd ed. (1992)), include *E. coli* helicase I, II, III, & IV, Rep, DnaB, PriA, PcrA, T4 Gp41helicase, T4 Dda helicase, T7 Gp4 helicases, SV40 Large T antigen, yeast RAD. Additional helicases that may be useful include RecQ helicase (Harmon and Kowalczykowski, J. Biol. Chem. 276:232 243 (2001)), thermostable UvrD helicases from *T. tengcongensis* and *T. thermophilus* (Collins and McCarthy, Extremophiles. 7:35 41. (2003)), thermostable DnaB helicase from *T. aquaticus* (Kaplan and Steitz, J. Biol. Chem. 274:6889 6897 (1999)), and MCM helicase from archaeal and eukaryotic organisms ((Grainge et al., Nucleic Acids Res. 31:4888 4898 (2003)).

Examples of helicases for use in present embodiments may also be found at the following web address: http://blocks.fh-crc.org (Get Blocks by Keyword: helicase). This site lists 49 Herpes helicases, 224 DnaB helicases, 250 UvrD-helicases and UvrD/Rep helicases, 276 DEAH_ATP-dependent helicases, 147 Papillom_E1 Papillomavirus helicase E1 protein, 608 Viral helicase1 Viral (superfamily 1) RNA helicases and 556 DEAD_ATP-dependent helicases. Examples of helicases that generally replicate in a 5' to 3' direction are T7 Gp4 helicase, DnaB helicase and Rho helicase, while examples of helicases that replicate in the 3'-5' direction include UvrD helicase, PcrA, Rep, NS3 RNA helicase of HCV.

Helicases use the energy of nucleoside triphosphate (for example ATP) hydrolysis to break the hydrogen bonds that hold the strands together in duplex DNA and RNA (Kornberg and Baker, DNA Replication, W.H. Freeman and Company (1992), especially chapter 11). Helicases are involved in every aspect of nucleic acid metabolism in the cell such as DNA replication, DNA repair and recombination, transcription, and RNA processing. This widespread usage may be reflected by the large numbers of helicases found in all living organisms.

Helicases have been classified according to a number of different characteristics. For example, a feature of different helicases is their oligomeric structure including helicases with single or multimeric structures. For example, one family of helicases is characterized by hexameric structures while another family consists of monomeric or dimeric helicases.

Another characteristic of helicases is the occurrence of conserved motifs. All helicases have the classical Walker A and B motifs, associated with ATP-binding and $Mg^{2+}$-binding (reviewed in Caruthers and McKay. Curr. Opin. Struct. Biol. 12:123 133 (2002), Soultanas and Wigley. Trends Biochem. Sci. 26:47 54 (2001)). Helicases have been classified into several superfamilies (Gorbalenya and Koonin. Curr. Opin. Struct. Biol. 3:419 429 (1993)) according to the number of helicase signature motifs and differences in the consensus sequences for motifs. Superfamilies 1 and 2 have seven characteristic helicase signature motifs and include helicases from archaea, eubacteria, eukaryotes and viruses, with helicases unwinding duplex DNA or RNA in either 3' to 5' direction or 5' to 3' direction. Examples of superfamily 1 helicases include the *E. coli* UvrD helicase, the *T. tengcongensis* UvrD helicase, and the B subunit of RecBCD. Superfamily 3 has three motifs and superfamily 4 has five motifs. Examples of superfamily 4 helicases include the T7 Gp4 helicase and DnaB helicases. A new family different from those canonical helicases is the AAA+ family (the extended family of ATPase associated with various cellular activities).

A third type of classification relates to the unwinding directionality of helicases i.e. whether the helicase unwinds the nucleic acid duplex in a 5'-3' direction (such as T7 Gp4 helicase) or in a 3'-5' direction (such UvrD helicase) based on the strand on which the helicase binds and travels.

A fourth type of classification relates to whether a helicase preferably unwinds blunt ended nucleic acid duplexes or duplexes with forks or single stranded tails. Blunt-ended nucleic acid duplexes may not be required in the first cycle of helicase-dependent amplification but are desirable in subsequent cycles of amplification because along with the progress of the amplification reaction the blunt-ended target fragment becomes the dominant species. These blunt-ended target nucleic acids form template substrates for subsequent rounds of amplification.

In general, the temperature for suitable denaturation may occur over a range of temperatures, for example 20° C. to 75° C. For example, temperature may be selected according to which helicase is selected for the melting process. Tests to determine optimum temperatures of a selected helicase can be determined by routine experimentation by varying the temperature of the reaction mixture and comparing products.

Denaturation of nucleic acid hybrids or duplexes can be accelerated by using a thermostable helicase preparation under incubation conditions that include higher temperature for example in a range of 45° C. to 75° C.

In certain aspects, it may be desirable to utilize a plurality of different helicase enzymes. For example, a helicase that has low processivity but is able to melt blunt-ended DNA may be combined with a second helicase that has great processivity but recognizes single-stranded tails at the border of duplex region for the initiation of unwinding. In this example, the first helicase initially separates the blunt ends of a long nucleic acid duplex generating 5' and 3' single-stranded tails and then dissociates from that substrate due to its limited processivity. This partially unwound substrate is subsequently recognized by the second helicase that then continues the unwinding process with superior processivity. In this way, a long target in a nucleic acid duplex may be unwound by the use of a helicase preparation containing a plurality of helicases.

D. Detection Labels

To aid in detection and quantitation of helicase activity, detection labels can be utilized. Detection labels can be directly incorporated into trap oligonucleotides, into one or both of the nucleic acid duplex nucleic acid strands. As used herein, a "detection label" is any molecule that can be associated with an oligonucleotide (e.g. trap oligonucleotides or one or both of the nucleic acid duplex nucleic acid strands) directly or indirectly, and which results in a measurable, detectable signal, either directly or indirectly. Many such labels for incorporation into nucleic acids or coupling to nucleic acids are known to those of skill in the art. Examples of detection labels suitable for use in the disclosed method are radioactive isotopes, fluorescent molecules, phosphorescent molecules, enzymes, antibodies, and ligands. Fluorescent labels, especially in the context of fluorescent change probes and primers, are useful for real-time detection of amplification.

Examples of suitable fluorescent labels include fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions such as quantum Dye™, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—CH3, Diamino Phenyl Oxydiazole (DAO), Dimethylamino-5-Sulphonic acid, Dipyrrometheneboron Difluoride, Diphenyl Brilliant Ravine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

Examples of fluorescent labels include fluorescein (5-carboxyfluorescein-N-hydroxysuccinimide ester), rhodamine (5,6-tetramethyl rhodamine), and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. Other examples of fluorescein dyes include 6-carboxyfluorescein (6-FAM), 2',4',1,4,-tetrachlorofluorescein (TET), 2',4',5',7',1,4-hexachlorofluorescein (HEX), 2',7'-dimethoxy-4',5'-dichloro-6-carboxyrhodamine (JOE), 2'-chloro-5'-fluoro-7',8'-fused phenyl-1,4-dichloro-6-carboxyfluorescein (NED), and 2'-chloro-7'-phenyl-1,4-dichloro-6-carboxyfluorescein (VIC). Fluorescent labels can be obtained from a variety of commercial sources, including Amersham Pharmacia Biotech, Piscataway, N.J.; Molecular Probes, Eugene, Oreg.; and Research Organics, Cleveland, Ohio.

Additional labels of interest include those that provide for signal only when the oligonucleotide with which they are associated is specifically bound to a target molecule (e.g. one of he nucleic acid strands of a nucleic acid duplex), where such labels include: "molecular beacons" as described in Tyagi & Kramer, Nature Biotechnology (1996) 14:303 and EP 0 070 685 B1. Other labels of interest include those described in U.S. Pat. No. 5,563,037 and PCT Applications WO 97/17471 and WO 97/17076.

Labeled nucleotides are another form of detection label since they can be directly incorporated into nucleic acid. Examples of detection labels that can be incorporated into nucleic acids include nucleotide analogs such as BrdUrd (5-bromodeoxyuridine, Hoy and Schimke, Mutation Research 290:217-230 (1993)), aminoallyldeoxyuridine (Henegariu et al., Nature Biotechnology 18:345-348 (2000)), 5-methylcytosine (Sano et al., Biochim Biophys. Acta 951: 157-165 (1988)), bromouridine (Wansick et al., J. Cell Biology 122:283-293 (1993)) and nucleotides modified with biotin (Langer et al., Proc. Natl. Acad. Sci. USA 78:6633 (1981)) or with suitable haptens such as digoxygenin (Kerkhof, Anal. Biochem. 205:359-364 (1992)). Suitable fluorescence-labeled nucleotides are Fluorescein-isothiocyanate-dUTP, Cyanine-3-dUTP and Cyanine-5-dUTP (Yu et al., Nucleic Acids Res., 22:3226-3232 (1994)). A preferred nucleotide analog detection label for DNA is BrdUrd (bromodeoxyuridine, BrdU, BUdR, Sigma-Aldrich Co). Other preferred nucleotide analogs for incorporation of detection label into DNA are AA-dUTP (aminoallyl-deoxyuridine triphosphate, Sigma-Aldrich Co.), and 5-methyl-dCTP (Roche Molecular Biochemicals). A preferred nucleotide analog for incorporation of detection label into RNA is biotin-16-UTP (biotin-16-uridine-5'-triphosphate, Roche Molecular Biochemicals). Fluorescein, Cy3, and Cy5 can be linked to dUTP for direct labeling. Cy3.5 and Cy7 are available as avidin or anti-digoxygenin conjugates for secondary detection of biotin- or digoxygenin-labeled probes.

Detection labels that are incorporated into nucleic acid, such as biotin, can be subsequently detected using sensitive methods well-known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2,-dioxetane-3-2'-(5'-chloro)tricyclo [3.3.1.13,7]decane]-4-yl)phenyl phosphate; Tropix, Inc.). Labels can also be enzymes, such as alkaline phosphatase, soybean peroxidase, horseradish peroxidase and polymerases, that can be detected, for example, with chemical signal amplification or by using a substrate to the enzyme which produces light (for example, a chemiluminescent 1,2-dioxetane substrate) or fluorescent signal. Labels can also be the disclosed reagent compositions.

Molecules that combine two or more of these detection labels are also considered detection labels. Any of the known detection labels can be used with the disclosed probes, tags, and method to label and detect target nucleic acid using the disclosed method. Methods for detecting and measuring signals generated by detection labels are also known to those of skill in the art. For example, radioactive isotopes can be detected by scintillation counting or direct visualization; fluorescent molecules can be detected with fluorescent spectrophotometers; phosphorescent molecules can be detected with a spectrophotometer or directly visualized with a camera; enzymes can be detected by detection or visualization of the product of a reaction catalyzed by the enzyme; antibodies can be detected by detecting a secondary detection label coupled to the antibody. As used herein, detection molecules are molecules which interact with nucleic acid and to which one or more detection labels are coupled.

Fluorescent Change Molecules

Fluorescent change molecules refer to all nucleic acid labels that involve a change in fluorescence intensity or wavelength based on a change in the form or conformation of the nucleic acid to be detected, assayed or replicated. Examples of fluorescent change molecules include molecular beacons, Amplifluors, FRET probes, cleavable FRET probes, TaqMan probes, scorpion primers, fluorescent triplex oligos including but not limited to triplex molecular beacons or triplex FRET probes, fluorescent water-soluble conjugated polymers, PNA probes, and QPNA probes. DxS' Scorpion Primers as described in U.S. Pat. No. 7,445,900; Whitcombe, et al, 1999, Nature Biotech 17, 804-807; Thelwell, et al. (2000), Nucleic Acid Research 29, 3752-3761; Solinas, et al. (2001), Nucleic Acid Research 29, 1-9, all of which are hereby incorporated by reference for their teaching of Scorpion primers, can also be used.

Fluorescent change molecules can be classified according to their structure and/or function. Fluorescent change probes include hairpin quenched probes, cleavage quenched probes, cleavage activated probes, and fluorescent activated probes. The use of several types of fluorescent change probes and primers are reviewed in Schweitzer and Kingsmore, Cum Opin. Biotech. 12:21-27 (2001). Hall et al., Proc. Natl. Acad. Sci. USA 97:8272-8277 (2000), describe the use of fluorescent change probes with Invader assays.

Hairpin quenched probes are probes that when not bound to a target sequence form a hairpin structure (and, typically, a loop) that brings a fluorescent label and a quenching moiety into proximity such that fluorescence from the label is quenched. When the probe binds to a target sequence, the stem is disrupted, the quenching moiety is no longer in proximity to the fluorescent label and fluorescence increases. Examples of hairpin quenched probes are molecular beacons, fluorescent triplex oligos, triplex molecular beacons, triplex FRET probes, and QPNA probes.

Cleavage activated probes are probes where fluorescence is increased by cleavage of the probe. Cleavage activated probes can include a fluorescent label and a quenching moiety in proximity such that fluorescence from the label is quenched. When the probe is clipped or digested (typically by the 5'-3' exonuclease activity of a polymerase during amplification), the quenching moiety is no longer in proximity to the fluorescent label and fluorescence increases. TaqMan probes (Holland et al., Proc. Natl. Acad. Sci. USA 88:7276-7280 (1991)) are an example of cleavage activated probes.

Modified TaqMan Probes

Also described herein are modified TaqMan probes. TaqMan probes are fluorescent change probes that involve a change in fluorescence intensity or wavelength based on a change in the form or conformation of the probe or primer and nucleic acid to be detected, assayed or replicated. For example, described herein are modified TaqMan probes that are comprised of a sequence that is complementary to a target sequence (e.g. one of the two nucleic acid strands of a nucleic acid duplex) and additionally have a short tail at either the 3' or 5'-end of the modified TaqMan probe complementary to the 5' or 3'-end modified TaqMan probe, respectively. The short tail can assist in forming a stem-loop structure when the modified TaqMan probe is not hybridized to a target nucleic acid. The non-tail portion of the modified TaqMan probe is complementary to the target nucleic acid and is capable of hybridizing to a target nucleic acid. In some aspects, the short tail of the modified TaqMan probe can be complementary or non-complementary to the target.

The modified TaqMan probes can be used as a detection label in the methods described herein. The modified TaqMan probes are an improvement of molecular beacons and existing TaqMan probes as they are easier to open than a molecular beacon and the modified TaqMan probes quench more predictably and efficiently than existing TaqMan probes.

Cleavage quenched probes can also be used in the methods described herein. Cleavage quenched probes are probes where fluorescence is decreased or altered by cleavage of the probe. Cleavage quenched probes can include an acceptor fluorescent label and a donor moiety such that, when the acceptor and donor are in proximity, fluorescence resonance energy transfer from the donor to the acceptor causes the acceptor to fluoresce. The probes are thus fluorescent, for example, when hybridized to a target sequence. When the probe is clipped or digested, the donor moiety is no longer in proximity to the acceptor fluorescent label and fluorescence from the acceptor decreases. If the donor moiety is itself a fluorescent label, it can release energy as fluorescence (typically at a different wavelength than the fluorescence of the acceptor) when not in proximity to an acceptor. The overall effect would then be a reduction of acceptor fluorescence and an increase in donor fluorescence. Donor fluorescence in the case of cleavage quenched probes is equivalent to fluorescence generated by cleavage activated probes with the acceptor being the quenching moiety and the donor being the fluorescent label. Cleavable FRET (fluorescence resonance energy transfer) probes are an example of cleavage quenched probes.

Fluorescent activated probes are probes or pairs of probes where fluorescence is increased or altered by hybridization of the probe to a target sequence. Fluorescent activated probes can include an acceptor fluorescent label and a donor moiety such that, when the acceptor and donor are in proximity (when the probes are hybridized to a target sequence), fluorescence resonance energy transfer from the donor to the acceptor causes the acceptor to fluoresce. Fluorescent activated probes are typically pairs of probes designed to hybridize to adjacent sequences such that the acceptor and donor are brought into proximity Fluorescent activated probes can also be single probes containing both a donor and acceptor where, when the probe is not hybridized to a target sequence, the donor and acceptor are not in proximity but where the donor and acceptor are brought into proximity when the probe hybridized to a target sequence. This can be accomplished, for example, by placing the donor and acceptor on opposite ends a the probe and placing target complement sequences at each end of the probe where the target complement sequences are complementary to adjacent sequences in a target sequence. If the donor moiety of a fluorescent activated probe is itself a fluorescent label, it can release energy as fluorescence (typically at a different wavelength than the fluorescence of the acceptor) when not in proximity to an acceptor (that is, when the probes are not hybridized to the target sequence). When the probes hybridize to a target sequence, the overall effect would then be a reduction of donor fluorescence and an increase in acceptor fluorescence. FRET probes are an example of fluorescent activated probes.

E. Solid Supports

Solid supports are solid-state substrates or supports with which nucleic acids (or other components used in, or produced by, the disclosed method) can be associated. The nucleic acids described herein can be associated with solid supports directly of indirectly to immobilize nucleic acids and/or oligonucleotides. For example, one or more of the nucleic acid strands of a nucleic acid duplex and/or a trap oligonucleotides can be associated with solid supports directly or indirectly. Oligonucleotides can be bound to the surface of a solid support or associated with oligonucleotide probes immobilized on solid supports. An array detector is a solid support to which multiple oligonucleotide probes can be coupled in an array, grid, or other organized pattern. Target arrays are arrays of target nucleic acids attached to solid supports. Oligonucleotide probe arrays are arrays of oligonucleotide probes attached to a solid support.

Solid-state substrates for use in solid supports can include any solid material with which components can be associated, directly or indirectly. This includes materials such as acrylamide, agarose, cellulose, nitrocellulose, glass, gold, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, functionalized silane, polypropylfumerate, collagen, glycosaminoglycans, polyamino acids or magnets. Solid-state substrates can have any useful form including thin film, membrane, bottles, dishes, fibers, woven fibers, shaped polymers, particles, beads, microparticles, or a combination. Solid-state substrates and solid supports can be porous or non-porous. A chip is a rectangular or square small piece of material. A useful form for a solid-state substrate is a microtiter dish. In some embodiments, a multiwell glass slide can be employed.

An array can include a plurality of components (such as target nucleic acids, target samples, detection labels, trap oligonucleotides) immobilized at identified or predefined locations on the solid support. Each predefined location on the solid support generally has one type of component (that is, all the components at that location are the same). Alternatively, multiple types of components can be immobilized in the same predefined location on a solid support. Each location will have multiple copies of the given components. The spatial separation of different components on the solid support allows separate detection and identification of nucleic acids. Although useful, it is not required that the solid support be a single unit or structure. Sets of components can be distributed over any number of solid supports. For example, at one extreme, each component can be immobilized in a separate reaction tube or container, or on separate beads or microparticles.

Methods for immobilization of oligonucleotides to solid-state substrates are well established. Oligonucleotides, including trap oligonucleotides, can be coupled to substrates using established coupling methods. For example, suitable attachment methods are described by Pease et al., Proc. Natl. Acad. Sci. USA 91(11):5022-5026 (1994), and Khrapko et al., Mol Biol (Mosk) (USSR) 25:718-730 (1991). A method for immobilization of 3'-amine oligonucleotides on casein-coated slides is described by Stimpson et al., Proc. Natl. Acad. Sci. USA 92:6379-6383 (1995). A useful method of attaching oligonucleotides to solid-state substrates is described by Guo et al., Nucleic Acids Res. 22:5456-5465 (1994).

Methods for immobilizing oligonucleotides to solid-state substrates are well established. Immobilization can be accomplished by attachment, for example, to aminated surfaces, carboxylated surfaces or hydroxylated surfaces using standard immobilization chemistries. Examples of attachment agents are cyanogen bromide, succinimide, aldehydes, tosyl chloride, avidin-biotin, photocrosslinkable agents, epoxides and maleimides. Another example of an attachment agent is glutaraldehyde. These and other attachment agents, as well as methods for their use in attachment, are described in Protein immobilization: fundamentals and applications, Richard F. Taylor, ed. (M. Dekker, New York, 1991), Johnstone and Thorpe, Immunochemistry In Practice (Blackwell Scientific Publications, Oxford, England, 1987) pages 209-216 and 241-242, and Immobilized Affinity Ligands, Craig T. Hermanson et al., eds. (Academic Press, New York, 1992).

Each of the components immobilized on the solid support can be located in a different predefined region of the solid support. The different locations can be different reaction chambers. Each of the different predefined regions can be physically separated from each other of the different regions. The distance between the different predefined regions of the solid support can be either fixed or variable. For example, in an array, each of the components can be arranged at fixed distances from each other, while components associated with beads will not be in a fixed spatial relationship. In particular, the use of multiple solid support units (for example, multiple beads) will result in variable distances.

Components can be associated or immobilized on a solid support at any density. Components can be immobilized to the solid support at a density exceeding 400 different components per cubic centimeter. Arrays of components can have any number of components. For example, an array can have at least 1,000 different components immobilized on the solid support, at least 10,000 different components immobilized on the solid support, at least 100,000 different components immobilized on the solid support, or at least 1,000,000 different components immobilized on the solid support.

E. Solid-State Detectors

Solid-state detectors are solid supports to which oligonucleotides, target nucleic acids, trap oligonucleotides, one or more nucleic acids strands of a nucleic acid duplex have been coupled. A preferred form of solid-state detector is an array detector. An array detector is a solid-state detector to which multiple different oligonucleotides or nucleic acids have been coupled in an array, grid, or other organized pattern.

Solid-state substrates for use in solid-state detectors can include any solid material to which oligonucleotides can be coupled. This includes materials such as acrylamide, agarose, cellulose, nitrocellulose, glass, gold, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, functionalized silane, polypropylfumerate, collagen, glycosaminoglycans, and polyamino acids. Solid-state substrates can have any useful form including thin film, membrane, bottles, dishes, fibers, woven fibers, shaped polymers, particles, beads, microparticles, or a combination. Solid-state substrates and solid supports can be porous or non-porous. A chip is a rectangular or square small piece of material. Preferred forms for solid-state substrates are thin films, beads, or chips. A useful form for a solid-state substrate is a microtiter dish. In some embodiments, a multiwell glass slide can be employed.

Capture oligonucleotides immobilized on a solid-state substrate allow capture of double-stranded probe-target hybrids or their amplification targets on a solid-state detector. Such capture provides a convenient means of washing away reaction components that might interfere with subsequent method steps. By attaching different capture oligonucleotides to different regions of a solid-state detector, different products can be captured at different, and therefore diagnostic, locations on the solid-state detector. For example, in a multiplex assay, oligonucleotides specific for numerous different target nucleic acids (each representing a different target nucleic acid sequence amplified via a different set of primers) can be immobilized in an array, each in a different location. Capture and detection will occur only at those array locations corresponding to amplified nucleic acids for which the corresponding target nucleic acid sequences were present in a sample.

F. Oligonucleotide Synthesis

Trap oligonucleotides or any other oligonucleotides can be synthesized using established oligonucleotide synthesis methods. Methods to produce or synthesize oligonucleotides are well known. Such methods can range from standard enzymatic digestion followed by nucleotide fragment isolation (see for example, Sambrook et al., Molecular Cloning: A Laboratory Manual, 2nd Edition (Cold Spring Harbor Laboratory Press, Cold Spring Harbor, N.Y., 1989) Chapters 5, 6) to purely synthetic methods, for example, by the cyanoethyl phosphoramidite method. Solid phase chemical synthesis of DNA fragments is routinely performed using protected nucleoside cyanoethyl phosphoramidites (S. L. Beaucage et al. (1981) Tetrahedron Lett. 22:1859). In this approach, the 3'-hydroxyl group of an initial 5'-protected nucleoside is first covalently attached to the polymer support (R. C. Pless et al. (1975) Nucleic Acids Res. 2:773 (1975)). Synthesis of the oligonucleotide then proceeds by deprotection of the 5'-hydroxyl group of the attached nucleoside, followed by coupling of an incoming nucleoside-3'-phosphoramidite to the deprotected hydroxyl group (M. D. Matteucci et al. (1981) J. Am. Chem. Soc. 103:3185). The resulting phosphite triester is finally oxidized to a phosphorotriester to complete the internucleotide bond (R. L. Letsinger et al. (1976) J. Am. Chem. Soc. 9:3655). Alternatively, the synthesis of phosphorothioate linkages can be carried out by sulfurization of the phosphite triester. Several chemicals can be used to perform this reaction, among them 3H-1,2-benzodithiole-3-one, 1,1-dioxide (R. P. Iyer, W. Egan, J. B. Regan, and S. L. Beaucage, J. Am. Chem. Soc., 1990, 112, 1253-1254). The steps of deprotection, coupling and oxidation are repeated until an oligonucleotide of the desired length and sequence is obtained. Other methods exist to generate oligonucleotides such as the H-phosphonate method (Hall et al, (1957) J. Chem. Soc., 3291-3296) or the phosphotriester method as described by Ikuta et al., Ann. Rev. Biochem. 53:323-356 (1984), (phosphotriester and phosphite-triester methods), and Narang et al., Methods Enzymol., 65:610-620 (1980), (phosphotriester method). Protein nucleic acid molecules can be made using known methods such as those described by Nielsen et al., Bioconjug. Chem. 5:3-7 (1994). Other forms of oligonucleotide synthesis are described in U.S. Pat. No. 6,294,664 and U.S. Pat. No. 6,291,669.

The nucleotide sequence of an oligonucleotide is generally determined by the sequential order in which subunits of subunit blocks are added to the oligonucleotide chain during synthesis. Each round of addition can involve a different, specific nucleotide precursor, or a mixture of one or more different nucleotide precursors. In general, degenerate or random positions in an oligonucleotide can be produced by using a mixture of nucleotide precursors representing the range of nucleotides that can be present at that position. Thus, precursors for A and T can be included in the reaction for a particular position in an oligonucleotide if that position is to be degenerate for A and T. Precursors for all four nucleotides can be included for a fully degenerate or random position. Completely random oligonucleotides can be made by including all four nucleotide precursors in every round of synthesis. Degenerate oligonucleotides can also be made having different proportions of different nucleotides. Such oligonucleotides can be made, for example, by using different nucleotide precursors, in the desired proportions, in the reaction.

Many of the oligonucleotides described herein are designed to be complementary to certain portions of other oligonucleotides or nucleic acids such that stable hybrids can be formed between them. The stability of these hybrids can be calculated using known methods such as those described in Lesnick and Freier, Biochemistry 34:10807-10815 (1995), McGraw et al., Biotechniques 8:674-678 (1990), and Rychlik et al., Nucleic Acids Res. 18:6409-6412 (1990).

So long as their relevant function is maintained, oligonucleotides can be made up of or include modified nucleotides (nucleotide analogs). Many modified nucleotides are known and can be used in oligonucleotides. A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl, hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Other modified bases are those that function as universal bases. Universal bases include 3-nitropyrrole and 5-nitroindole. Universal bases substitute for the normal bases but have no bias in base pairing. That is, universal bases can base pair with any other base. Base modifications often can be combined with for example a sugar modification, such as 2'-O-methoxyethyl, to achieve unique properties such as increased duplex stability. There are numerous U.S. Pat. Nos. such as 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, which detail and describe a range of base modifications. Each of these patents is herein incorporated by reference in its entirety, and specifically for their description of base modifications, their synthesis, their use, and their incorporation into oligonucleotides and nucleic acids.

G. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example, disclosed is a kit comprising a nucleic acid duplex comprising two strands of nucleic acid where the first strand is immobilizable and the second strand is detectably labeled, a trap oligonucleotide, an immobilization substrate, wash buffers and a helicase. The kits also can contain, for example, nucleotides, buffers, helicase, accessory proteins, topoisomerases, or a combination.

H. Mixtures

Disclosed are mixtures formed by preparing the disclosed composition or performing or preparing to perform the disclosed methods. Whenever the method involves mixing or bringing into contact compositions or components or reagents, performing the method creates a number of different mixtures. For example, if the method includes 3 mixing steps, after each one of these steps a unique mixture is formed if the steps are performed separately. In addition, a mixture is formed at the completion of all of the steps regardless of how the steps were performed. The present disclosure contemplates these mixtures, obtained by the performance of the disclosed methods as well as mixtures containing any disclosed reagent, composition, or component, for example, disclosed herein.

I. Systems

Disclosed are systems useful for performing, or aiding in the performance of, the disclosed method. Also disclosed are systems for producing reagent compositions. Systems generally comprise combinations of articles of manufacture such as structures, machines, devices, and the like, and compositions, compounds, materials, and the like. Such combinations that are disclosed or that are apparent from the disclosure are contemplated. For example, disclosed and contemplated are systems comprising solid supports and reagent compositions.

J. Data Structures and Computer Control

Disclosed are data structures used in, generated by, or generated from, the disclosed method. Data structures generally are any form of data, information, and/or objects collected, organized, stored, and/or embodied in a composition or medium. A target fingerprint stored in electronic form, such as in RAM or on a storage disk, is a type of data structure.

The disclosed method, or any part thereof or preparation therefore, can be controlled, managed, or otherwise assisted by computer control. Such computer control can be accomplished by a computer controlled process or method, can use and/or generate data structures, and can use a computer program. Such computer control, computer controlled processes, data structures, and computer programs are contemplated and should be understood to be disclosed herein.

K. Uses

The disclosed compositions and methods are applicable to numerous areas including, but not limited to, detection and/or analysis of target nucleic acids, disease detection, protein detection, nucleic acid mapping, mutation detection, gene discovery, gene mapping, determination of helicase activity, and agricultural research. Particularly useful are assays to measure or determine helicase activity. For example, one of skill in the art can use the disclosed methods, assays, and compositions to determine which helicase is best to use with a given assay, whether a given helicase is working optimally, as well as which reaction conditions are best for a given helicase. Other uses include, for example, detection of target nucleic acids in samples, mutation detection; detection of sexually transmitted diseases such as *Chlamydia trachomatis* (CT) and *Neisseria gonorrhoea* (NG).

Methods

Disclosed herein are methods of measuring helicase activity comprising providing a nucleic acid duplex comprising a first immobilizable nucleic acid strand and a labeled second strand; immobilizing the nucleic acid duplex; contacting the immobilized nucleic acid substrate duplex with a helicase to form a helicase-duplex mixture; incubating the helicase-duplex mixture with a trap oligonucleotide under conditions for helicase activity; separating non-immobilized nucleic acids, and; detecting the label present with the immobilized nucleic acids, wherein a decrease in the amount of label present indicates helicase activity.

In one example, the amount of label present can be determined after the nucleic acid duplex is provided or after it is immobilized. The amount of label present can be determined again after incubation with the trap oligonucleotide and the washing step. This allows for a differential measurement in the amount of label present. A decrease in the amount of label indicates that there is helicase activity.

The trap oligonucleotide can be complementary to the first or second strand of the nucleic acid duplex, and they can form a duplex referred to as the trap-target duplex, for example. As described herein, by "complementary" is meant that the trap oligonucleotide recognizes and physically interacts (that is, base-pairs) with a substantially complementary nucleic acid (for example, the second strand of the nucleic acid duplex) under high stringency conditions, and does not substantially base pair with other nucleic acids.

A "decrease in the amount of label" means there is less label present after contact with the trap oligonucleotide and the washing step than before. The decrease can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%. This can indicate the amount of labeled nucleic acid removed during the washing step.

In one example, a duplex can form between the trap oligonucleotide and the labeled second strand. When this occurs, the trap oligonucleotide can be captured and the amount of label present with the trapped oligonucleotide can be determined as well. Alternatively, if the duplex formed between the trap oligonucleotide and the labeled second strand is washed away, the amount of label present in the wash can be determined as well.

The amount of helicase activity present can be quantified by the amount of label present. One of skill in the art can readily determine this by correlating activity with label. For example, a 5% decrease in label could indicate that the helicase is performing at 5%. In other words, if there are 100 strands of target present, a 5% decrease could indicate that that 95 out of 100 of the strands were not separated by helicase. One of skill in the art will further appreciate that background and unwashed label can be accounted for as well in quantifying helicase activity. No decrease in label could indicate that there is no helicase activity, while a 100% decrease in detected label (i.e., no label detected above background) could indicate that the helicase is 100% functional. Of course, to determine the specific percentage of activity can be affected by a number of factors including substrate concentration, enzyme concentration, etc. For example, if the substrate is in excess with relation to the enzyme, the exact percentage of enzyme activity could be higher than the amount of fluorescence due to the differing concentrations.

Any of the steps in the method outlined above can be carried out simultaneously or within a homogenous assay. For example, the steps of providing nucleic acid duplex, immobilizing the duplex, and contacting it with a helicase can all be preformed simultaneously.

Also disclosed is a method for measuring helicase activity comprising: providing a nucleic acid duplex comprising a first immobilizable nucleic acid strand and a labeled second strand; immobilizing the nucleic acid duplex; contacting the immobilized nucleic acid substrate duplex with a helicase to form a helicase-duplex mixture; incubating the helicase-duplex mixture with a trap oligonucleotide under conditions for helicase activity; separating non-immobilized nucleic acids, and detecting the amount of label present with the non-immobilized nucleic acids, wherein the presence of label over background indicates helicase activity.

In one example, the amount of label present can be determined after the nucleic acid duplex is provided. It can be determined again after incubation with the trap oligonucleotide and the washing step. This allows for a differential measurement in the amount of label present. The presence of any label over background can indicate that there is helicase activity.

Further disclosed is a method of measuring helicase activity comprising: providing a nucleic acid duplex comprising a first immobilizable nucleic acid strand and a labeled second strand; contacting the immobilized nucleic acid substrate duplex with a helicase to form a helicase-duplex mixture; incubating the helicase-duplex mixture with a trap oligonucleotide under conditions for helicase activity; immobilizing the first immobilizable strand of the nucleic acid duplex, separating non-immobilized nucleic acids, and; detecting the label present with the immobilized nucleic acids, wherein a decrease in the amount of label present indicates helicase activity.

In this example, the immobilizable strand of the nucleic acid duplex is immobilized after the helicase-duplex mixture has been incubated with the trap oligonucleotide. One of skill in the art will appreciate that the immobilizable nucleic acid can be immobilized at any point during the method.

Also disclosed are methods of measuring helicase activity comprising: providing a nucleic acid duplex comprising a first nucleic acid strand and a labeled second strand; contacting the nucleic acid substrate duplex of step a) with a helicase to form a helicase-duplex mixture; incubating the helicase-duplex mixture with an immobilizable trap oligonucleotide under conditions for helicase activity; immobilizing the immobilizable trap oligonucleotide; separating non-immobilized nucleic acids, and; detecting the label present with immobilized trap oligonucleotide, wherein an increase in the amount of label present indicates helicase activity.

Again, one of skill in the art will appreciate that the trap oligonucleotide can be immobilized at any point during the method described. It can happen before, during, or after the trap oligonucleotide forms a duplex with the labeled second strand of the nucleic acid duplex.

Also disclosed are methods of measuring helicase activity comprising: providing a nucleic acid duplex comprising a first immobilizable nucleic acid strand and a labeled second strand; contacting the nucleic acid substrate duplex of step a) with a helicase to form a helicase-duplex mixture; incubating the helicase-duplex mixture with an immobilizable trap oligonucleotide under conditions for helicase activity; immobilizing the immobilizable trap oligonucleotide; separating the immobilized first immobilizable nucleic acid strand from the immobilizable trap oligonucleotide, and; detecting the label present with the immobilized trap oligonucleotide, wherein an increase in the amount of label present indicates helicase activity.

Also disclosed are methods of measuring helicase activity comprising: providing a nucleic acid duplex comprising a first immobilizable nucleic acid strand and a labeled second strand; contacting the nucleic acid substrate duplex of step a) with a helicase to form a helicase-duplex mixture; incubating the helicase-duplex mixture with an immobilizable trap oligonucleotide under conditions for helicase activity; immobilizing the immobilizable trap oligonucleotide; separating the immobilized first immobilizable nucleic acid strand from the immobilizable trap oligonucleotide, and; detecting the label present with immobilized first immobilizable nucleic acid strand, wherein a decrease in the amount of label present indicates helicase activity.

Further disclosed are methods for measuring helicase activity comprising: providing a nucleic acid duplex comprising a first nucleic acid strand and a second nucleic acid strand; determining the amount of label present; contacting the nucleic acid duplex with a helicase to form a helicase-duplex mixture; incubating the helicase-duplex mixture with a trap oligonucleotide under conditions for helicase activity, wherein the trap oligonucleotide comprises a fluorescent change probe portion; and detecting the label present in the mixture, wherein an increase in the amount of label present indicates helicase activity. The above method can be conducted in an entirely closed, or homogenous, assay.

The fluorescent change probe portion of the trap oligonucleotide acts as a fluorescent activated probes. The fluorescent activated probe portion is a portion of the trap oligonucleotide where fluorescence is increased or altered by hybridization of the trap oligonucleotide to an oligonucleotide that comprises a complementary sequence to the second strand of the nucleic acid duplex. The fluorescent activated probe portion can include an acceptor fluorescent label and a donor moiety such that, when the acceptor and donor are in proximity (when the probes are hybridized to a target sequence), fluorescence resonance energy transfer from the donor to the acceptor causes the acceptor to fluoresce. The fluorescent activated probe portion can be designed to hybridize to adjacent sequences such that the acceptor and donor are brought into proximity. The fluorescent activated probe portion can also be single oligonucleotide containing both a donor and acceptor where, when the trap oligonucleotide is not hybridized to a complementary sequence, the donor and acceptor are not in proximity but where the donor and acceptor are brought into proximity when the trap oligonucleotide hybridizes to a complementary sequence. This can be accomplished, for example, by placing the donor and acceptor on opposite ends of the trap oligonucleotide and placing target complement sequences at each end of the probe where the target complement sequences are complementary to adjacent sequences in a complementary sequence. If the donor moiety of a fluorescent activated probe is itself a fluorescent label, it can release energy as fluorescence (typically at a different wavelength than the fluorescence of the acceptor) when not in proximity to an acceptor (that is, when the probes are not hybridized to the target sequence). When the trap oligonucleotide hybridizes to a complementary sequence, the overall effect would then be a reduction of donor fluorescence and an increase in acceptor fluorescence. FRET probes are an example of fluorescent activated probes.

EXAMPLES

Example 1

Generally, some of the methods described herein comprise an annealing step to create a duplex substrate, binding of the substrate to the solid support, addition of helicase as trap oligo, washing, and detection. The following is an exemplary protocol employed in a fluorescent-based helicase assay.

Annealing of Duplex Oligos:
1) Dissolve each of the labeled complementary oligo in ThermoPol Buffer (20 mM, Tris-HCl, pH 8.8, 10 mM KCl, 10 mM $(NH_4)_2SO_4$, 2 mM $MgSO_4$, 0.1% Triton-X100).
2) Combine 75 nM of pHDAbio and 50 nM of pHDAcy3 in a 1.5 ml microfuge tube and incubate at 95° C. for 2 min on a heating block. Remove the tube from the heating block and cool down to room temperature by placing tube in rack on bench (approximately 70 mins) Place the tube in ice until further use. The reaction volume for each annealing reaction was 30 ul.

Attaching Annealed Mix to Streptavidin Coated Plate
3) Prewash the streptavidin coated plates with 200 ul wash buffer (25 mM Tris-HCl, pH 7.4, 0.05% Tween-20, 150 mM NaCl).
4) Add 30 ul of wash buffer to each 30 ul of the annealing reaction from step 2. Add the entire mix (60 ul) to the streptavidin coated plate.
5) Incubate the plate at RT for 30 min with shaking.

Addition of Helicase Mix
6) Remove the liquid and add different concentrations of Tte-UvrD Helicase and capture oligo (pHDAC) at a concentration of 800 nM in a total reaction volume of 50 ul in ThermoPol Buffer (20 mM, Tris-HCl, pH 8.8, 10 mM KCl, 10 mM $(NH_4)_2SO_4$, 2 mM $MgSO_4$, 0.1% Triton-X100). Pre-incubate at 65° C. for 2 min
7) Initiate the reaction by adding ATP to 3 mM and continue incubation at 65° C. for 10 min
8) Remove the liquid and wash the streptavidin coated plate three times with streptavidin wash buffer. Add 50 ul water to each well.
9) Incubate the plate at RT for 60 min with shaking.
10) Read the plate in a fluorescent plate reader with excitation of 535 nm and emission of 590 nm.

The concentration of Tte-UvrD Helicase used was 150 ng/uL, the MW of protein is 82.66 kDa, and 150 ng/uL of UvrD corresponds to approximately 1.8 uM. The concentration of substrate used was approximately 50 nM. The assay used between 5-100 nM of Helicase for the reaction in hopes of obtaining a linear plot. The different concentration points used were 0 nM, 5 nM, 10 nM, 25 nM, 50 nM, 100 nM.

Optionally, instead of water TE buffer may be used (10 mM Tris, 1 mM EDTA, brought to pH of approximately 7.5 to 8.0 with hydrochloric acid).

Table 1 shows a table of the reagents and materials used in an exemplary Fluorescent based Helicase Assay.

TABLE 1

Reagents and Materials for the Fluorescent based DNA Helicase Assay.

| Reagents and Equipment | Company | Catalog Number |
|---|---|---|
| 100 mM ATP | Amersham | 27-2056-01 |
| 100 mM dATP | Amersham | 27-2050-03 |
| pHDAcy3 | IDT | N/A |
| pHDAbio | IDT | N/A |
| pHDAC | IDT | N/A |
| Streptavidin Wash Buffer | N/A | N/A |
| ThermoPol Buffer | N/A | N/A |
| Reacti-Bind Streptavidin HBC coated 96-well black plates | Pierce | 15503 |
| Tte-UvrD Helicase | BioHelix | N/A |
| Tecan Fluorescent plate Reader | GeniosPro | S/N 05668 |
| Hybrid Capture Heating Blocks | Digene | |

Table 2 shows a table of the oligos used in the Helicase Assay. pHDAcy3 has a cy3 fluorophore at is 5' end and is complementary to pHDAbio, which has a biotin label at its 5' end. pHDAC, the trap oligo, consists of the same sequence as pHDAbio without the 5' biotin and therefore is complementary to pHDAcy3.

TABLE 2

The sequences of the oligonucleotides used in the Helicase Assay.

| Name | Sequence | SEQ. ID. NO.: |
|---|---|---|
| pHDAcy3 | 5' Cy3-AAT TGT TTC CAA ATG CAC TGG CCG TCG TTT TAC | 1 |
| pHDAbio | 5' Bio-GTA AAA CGA CGG CCA GTG CAT TTG GAA ACA ATT | 2 |
| pHDAC | 5' GTA AAA CGA CGG CCA GTG CAT TTG GAA ACA ATT | 3 |

Figure 3:
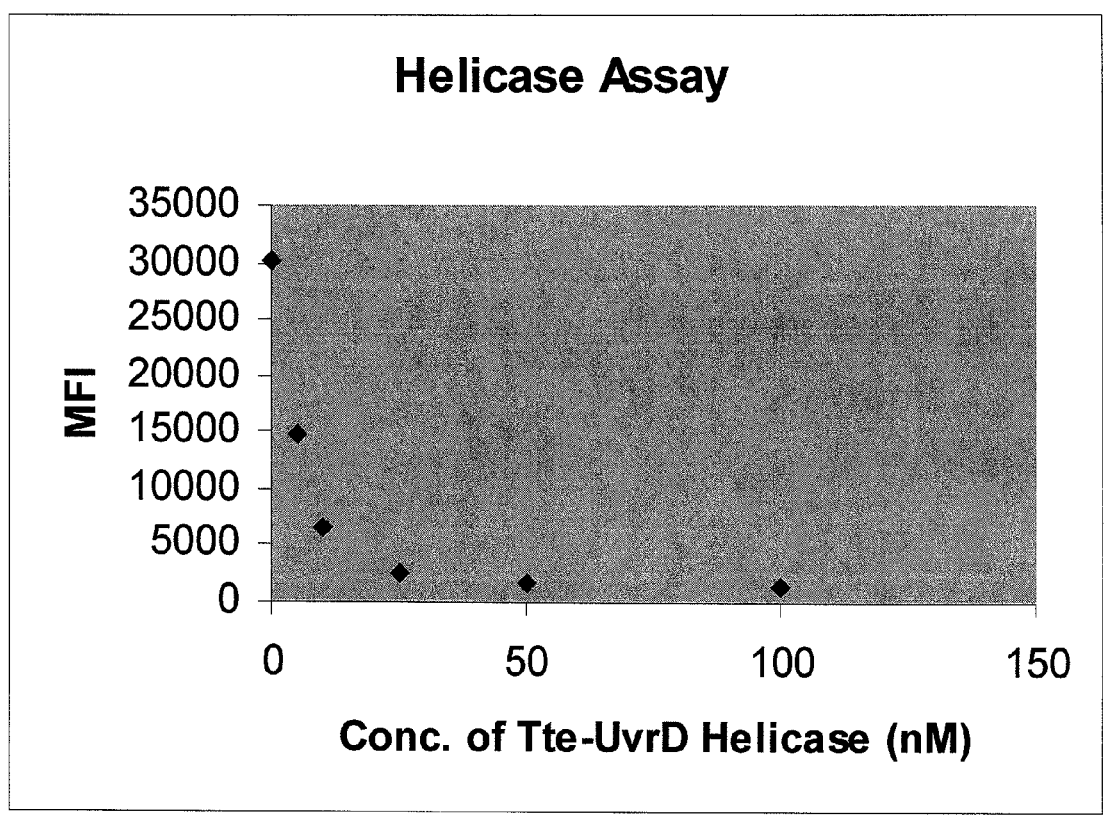
FIG. 3 is a plot of experimental results obtained using the helicase assay. The measurements are of material bound to the streptavidin coated pate, and the decrease in fluorescence represents the loss of the complementary labeled strand due to helicase activity (unwinding of the duplex).
Figure 4:
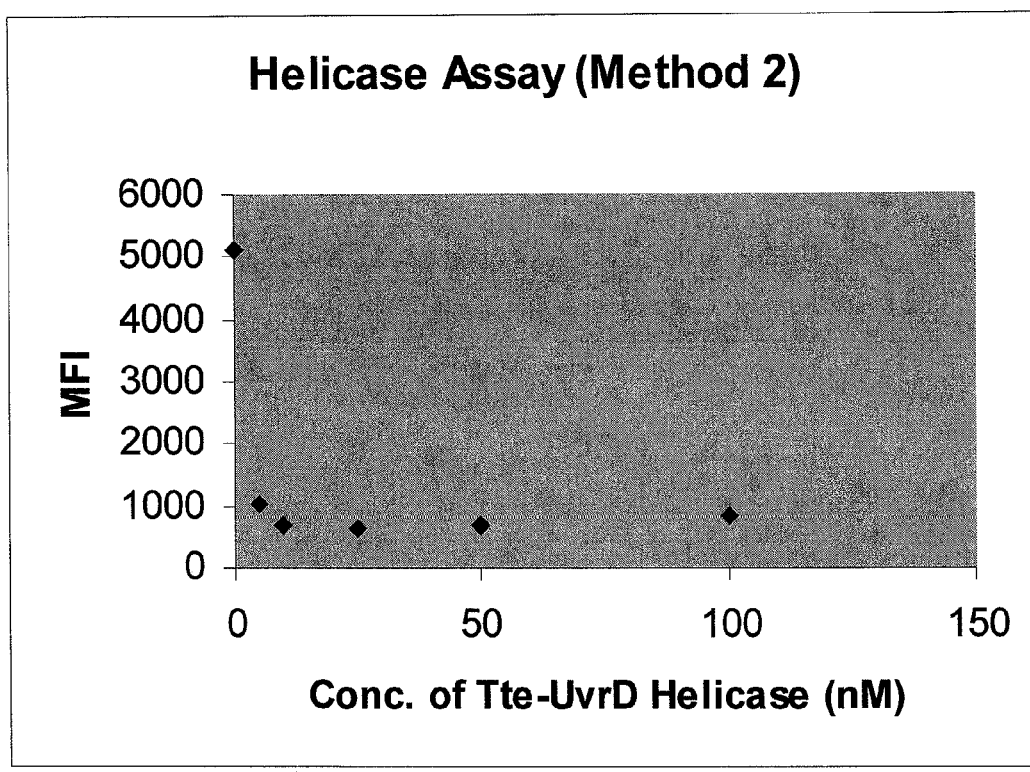
FIG. 4 is a plot of experimental results obtained using Method 2 of the helicase assay. The results are comparable to the results in FIG. 7.

FIG. 3 is a plot of the data obtained with this protocol. This reaction is dependent upon ATP as removal of ATP results in no activity seen. Also the trap oligo plays some role in ensuring that the unwound cy3 strand remains sequestered and does not re-associate with the biotinylated strand. The concentrations of Helicase used in this assay were outside of the linear range and thus the assay falls off very quickly.

Table 4 shows the data obtained using the above protocol. Because the assay measures the material bound to the streptavidin coated bioplate, one expects a decrease in fluorescence to represent the loss or unwinding of the complementary cy3 strand to the biotinylated strand.

TABLE 3

Constituency of the Buffers used in the Fluorescent based Helicase Assay.

| ThermoPol Buffer (Lot #022607NA) | Streptavidin Wash Buffer (Lot #120506NA) |
|---|---|
| 20 mM Tris-HCl, pH 8.8 | 25 mM Tris-HCl, pH 7.4 |
| 10 mM KCl | 0.05% Tween-20 |
| 10 mM $(NH_4)_2SO_4$ | 150 mM NaCl |
| 2 mM $MgSO_4$ | |
| 0.1% Triton-X100 | |

TABLE 4

Data obtained using Method 1 of the Helicase Assay. Data Analysis of Method 1

| Material | Fluorescence | MFI | Corrected MFI | Std. Dev | % CV |
|---|---|---|---|---|---|
| 0 nM Helicase | 34103 | 32362 | 30062 | 1554 | 5 |
| | 31870 | | | | |
| | 31114 | | | | |
| 5 nM Helicase | 16451 | 17090 | 14790 | 694 | 4 |
| | 17829 | | | | |
| | 16990 | | | | |
| 10 nM Helicase | 8630 | 8707 | 6407 | 976 | 11 |
| | 9719 | | | | |
| | 7771 | | | | |
| 25 nM Helicase | 4452 | 4858 | 2558 | 381 | 8 |
| | 5208 | | | | |
| | 4913 | | | | |
| 50 nM Helicase | 3825 | 3884 | 1584 | 144 | 4 |
| | 4049 | | | | |
| | 3779 | | | | |
| 100 nM Helicase | 3843 | 3815 | 1515 | 65 | 2 |
| | 3862 | | | | |
| | 3741 | | | | |
| 100 nM, NoATP | 43303 | 39766 | 37466 | 3214 | 8 |
| | 37024 | | | | |
| | 38970 | | | | |

TABLE 4-continued

Data obtained using Method 1 of the Helicase Assay. Data Analysis of Method 1

| Material | Fluorescence | MFI | Corrected MFI | Std. Dev | % CV |
|---|---|---|---|---|---|
| 100 nM, No pHDAC | 6537 | 6987 | 4687 | 542 | 8 |
| | 7589 | | | | |
| | 6835 | | | | |
| Oligo + Buffer | 46572 | 39014 | 36714 | 7351 | 19 |
| | 38582 | | | | |
| | 31889 | | | | |

TABLE 4-continued

Data obtained using Method 1 of the Helicase Assay.
Data Analysis of Method 1

| Material | Fluorescence | MFI | Corrected MFI | Std. Dev | % CV |
|---|---|---|---|---|---|
| No Oligo + buffer | 2282<br>2319<br>2299 | 2300 | 0 | 19 | 1 |

Example 2

The following is another protocol employed in the Fluorescent-based Helicase Assay. In this method, the Helicase Mix is added to the annealed duplex oligo solution in a regular 96 well plate. After the Helicase reaction has proceed for 10 min at 65° C., the mix is then transferred to the straptavidin coated bioplate.

Annealing of Duplex Oligos:
1) Dissolve each of the labeled complementary oligo in ThermoPol Buffer (20 mM, Tris-HCl, pH 8.8, 10 mM KCl, 10 mM $(NH_4)_2SO_4$, 2 mM $MgSO_4$, 0.1% Triton-X100).
2) Combine 75 nM of pHDAbio and 50 nM of pHDAcy3 in a 1.5 ml microfuge tube and incubate at 95° C. for 2 min on a heating block. Remove the tube from the heating block and cool down to room temperature by placing tube in rack on bench (approximately 70 mins). Place the tube in ice until further use. The reaction volume for each annealing reaction was 30 ul.

Addition of Helicase Mix
3) Mix the annealed oligos with 30 ul of differing amounts of Tte-UvrD Helicase and trap DNA at a concentration of 800 nM in ThermoPol Buffer in a regular 96 well plate, incubate this mix at 65° C. for 2 min
4) Initiate the reaction by adding ATP to 3 mM and continue incubation for 10 min at 65° C.

Attaching Reaction Mix to Streptavidin Coated Plate
5) Prewash the streptavidin coated plates with 200 ul wash buffer (25 mM Tris-HCl, pH 7.4, 0.05% Tween-20, 150 mM NaCl).
6) Add 60 ul of wash buffer to each of the wells of the regular 96 well plate. Transfer the entire mix to the streptavidin coated plate.
7) Incubate the plate at RT for 30 min with shaking.
8) Remove the liquid and wash the well three times with wash buffer. Add 50 ul water to each well.
9) Incubate the plate at RT for 60 min with shaking.
10) Read the plate in a fluorescent plate reader with excitation of 535 nm and emission of 590 nm.

FIG. 9 is a plot of the data obtained from using Helicase Assay Method 2. Note that the results are again outside of the linear range using these concentrations of Tte-UvrD Helicase. A comparison of Method 1 vs. Method 2 shows that they are very comparable in the data produced. Method 1 is less time-consuming than Method 2 and involves less sample transfer.

Table 5 presents data obtained using Method 2 and the results seen here coincide with the data seen in Method 1. ATP and the capture oligo play similar roles to that seen in Method 1. The pHDAC trap oligo has more dramatic effect on preventing re-annealing. Table 5: Data obtained using Method 2, the results seen here coincide greatly with the data seen in Method 1. ATP and the capture oligo play similar roles to that seen in Method 1. The pHDAC trap oligo has more dramatic effect on preventing re-annealing.

TABLE 5

Data Analysis of Method 2 (material left on plate, pellet)

| Material | Fluores. | Avg. Fluores. | Corrected MFI | Std. Dev | % CV |
|---|---|---|---|---|---|
| 0 nM | 5234<br>5516<br>5347 | 5366 | 5130 | 142 | 3 |
| 5 nM Helicase | 1075<br>902<br>1173 | 1050 | 1034 | 137 | 13 |
| 10 nM Helicase | 940<br>931<br>882 | 918 | 682 | 31 | 3 |
| 25 nM Helicase | 913<br>875<br>881 | 890 | 654 | 20 | 2 |
| 50 nM Helicase | 840<br>863<br>1027 | 910 | 675 | 102 | 11 |
| 100 nM Helicase | 1180<br>1132<br>944 | 1085 | 850 | 125 | 11 |
| 100 nM, NoATP | 6362<br>6302<br>6796 | 6487 | 6252 | 270 | 4 |
| 100 nM, No pHDAC | 6074<br>6632<br>8110 | 6939 | 6704 | 1052 | 15 |
| Oligo + Buffer | 7583<br>5806<br>5443 | 6277 | 6042 | 1145 | 18 |
| No oligo + buffer | 236<br>233<br>237 | 235 | 0 | 2 | 1 |

Example 3

Previous work using ATPase assays to assess the activity of Tte-UvrD helicase showed that Tte-UvrD Helicase achieved maximal activity at 55° C. and lost 30% of its ATPase activity after 90 minutes of continuous incubation at 65° C. The following protocol was utilized to assess the activity of the helicase at 55° C.

Annealing of Duplex Oligos:
1) Dissolve each of the labeled complementary oligo in ThermoPol Buffer (20 mM, Tris-HCl, pH 8.8, 10 mM KCl, 10 mM $(NH_4)_2SO_4$, 2 mM $MgSO_4$, 0.1% Triton-X100).
2) Combine 75 nM of pHDAbio dissolved oligo with 50 nM of pHDAcy3 dissolved oligo in a 1.5 mL microfuge tube and incubate at 95° C. for 2 min on a heating block. Remove the tube from the heating block and cool down to room temperature by placing tube in rack on bench (approximately 70-90 min). Place the tube in ice until further use. Keep the reaction tube containing cy3 in the dark as much as possible. The reaction volume for each annealing reaction was 30 ul.

Attaching Annealed Mix to Streptavidin Coated Plate
3) Prewash the streptavidin coated plates with 200 ul wash buffer (25 mM Tris-HCl, pH 7.4, 0.05% Tween-20, 150 mM NaCl).
4) Add 30 ul of wash buffer to each 30 ul of annealed oligo mix. Add the entire mix (60 ul total) to each well of the streptavidin coated plate.
5) Incubate the plate at RT for 30 min with shaking.

Addition of Helicase Mix
   6) Remove the liquid and wash the well three times with wash buffer. Add different concentrations of Tte-UvrD Helicase and capture oligo (pHDAC) at a concentration of 800 nM in a total reaction volume of 50 ul in ThermoPol Buffer (20 mM, Tris-HCl, pH 8.8, 10 mM KCl, 10 mM (NH$_4$)$_2$SO$_4$, 2 mM MgSO$_4$, 0.1% Triton-X100). Pre-incubate at 55° C. for 2 min
   7) Initiate the reaction by adding ATP to 3 mM and continue incubation at 55° C. for 10 min
   8) Transfer liquid to a regular U bottom hybridization plate until further use, make sure to keep the plate in the dark as much as possible.
   9) Wash the streptavidin coated plate three times with streptavidin wash buffer. Add 50 ul water to each well.
   10) Transfer the liquid from the U bottom hybridization plate to unused wells on the streptavidin coated plate (this represents the released cy3-strand from the helicase assay).
   11) Incubate the plate at RT for 60 min with shaking.
   12) Read the plate in a fluorescent plate reader with excitation of 535 nm and emission of 590 nm.

The concentration of Tte-UvrD Helicase used was between 2.5-20 nM, in the hopes of obtaining a linear plot. The different Helicase concentrations used include 0 nM, 2.5 nM, 5 nM, 10 nM, 15 nM, 20 nM.

Table 6 shows data obtained from the Helicase assay performed at 55° C. These values represent the material that remained bound to the streptavidin coated bioplate (pellet).

TABLE 6

Data obtained from performing the Helicase Assay at 55° C.
Helicase Assay (pellet) 030507NA

| Material | Fluorescence | MFI | Corrected MFI | Std. Dev. | % CV |
|---|---|---|---|---|---|
| 0 nM Helicase | 28317 28585 29191 | 28698 | 26849 | 448 | 2 |
| 2.5 nM Helicase | 23976 27682 25732 | 25797 | 23948 | 1854 | 7 |
| 5 nM Helicase | 23653 24985 26311 | 24983 | 23134 | 1329 | 5 |
| 10 nM Helicase | 25816 23298 24952 | 24689 | 22840 | 1279 | 5 |
| 15 nM Helicase | 26175 23004 23233 | 24137 | 22288 | 1768 | 7 |
| 20 nM Helicase | 21896 25157 22921 | 23325 | 21476 | 1668 | 7 |
| 20 nM, NoATP | 33326 31737 28753 | 31272 | 29423 | 2322 | 7 |
| 20 nM, No pHDAC | 27632 26593 26364 | 26863 | 25014 | 676 | 3 |
| Oligo + Buffer | 24053 33647 34253 | 30651 | 28802 | 5722 | 19 |
| 0 nM, no pHDAC | 28726 31029 29806 | 29854 | 28005 | 1152 | 4 |
| No Oligo + buffer | 1845 1921 1780 | 1849 | 0 | 71 | 4 |
| 1/10 reaction mix | 5954 5101 5619 | 5558 | 3709 | 430 | 8 |

TABLE 6-continued

Data obtained from performing the Helicase Assay at 55° C.
Helicase Assay (pellet) 030507NA

| Material | Fluorescence | MFI | Corrected MFI | Std. Dev. | % CV |
|---|---|---|---|---|---|
| 1/100 reaction mix | 2170 2228 2258 | 2219 | 370 | 45 | 2 |

Figure 5:
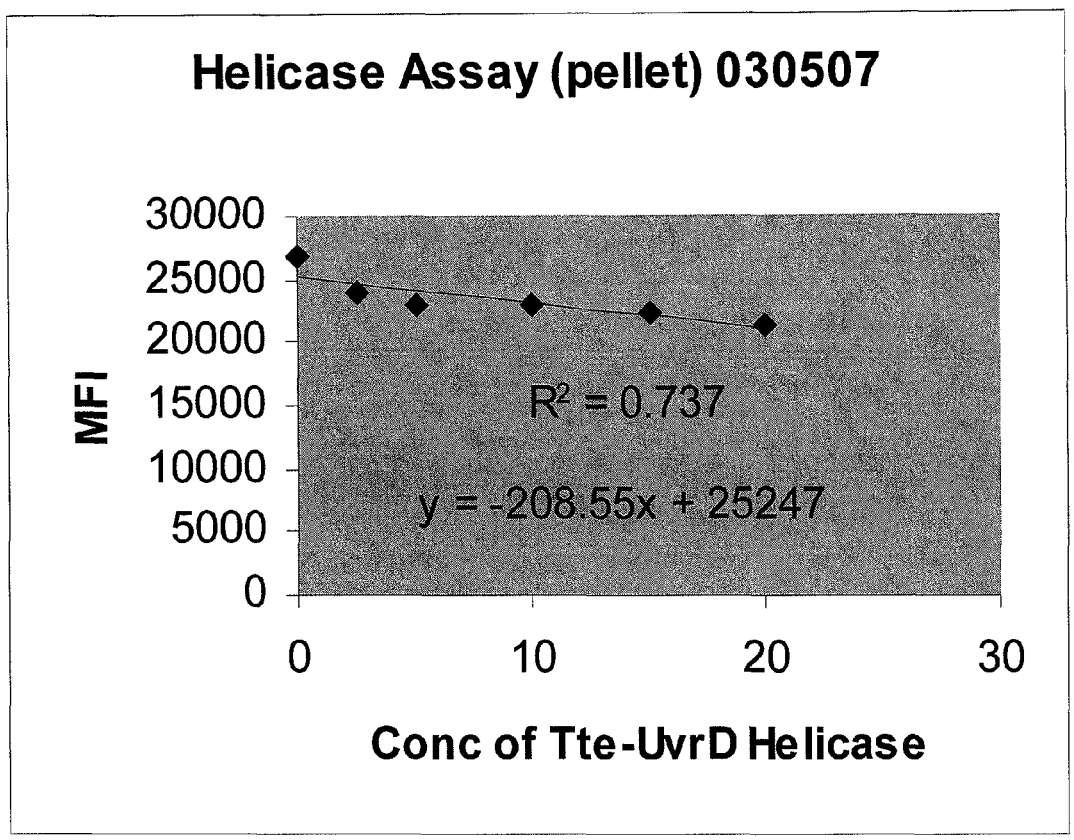
FIG. 5 depicts results from an experiment performance of the helicase assay at 55° C. On increasing helicase concentrations, there is a decrease in fluorescence of material bound to the plate, indicating an increase in helicase activity.
Figure 6:
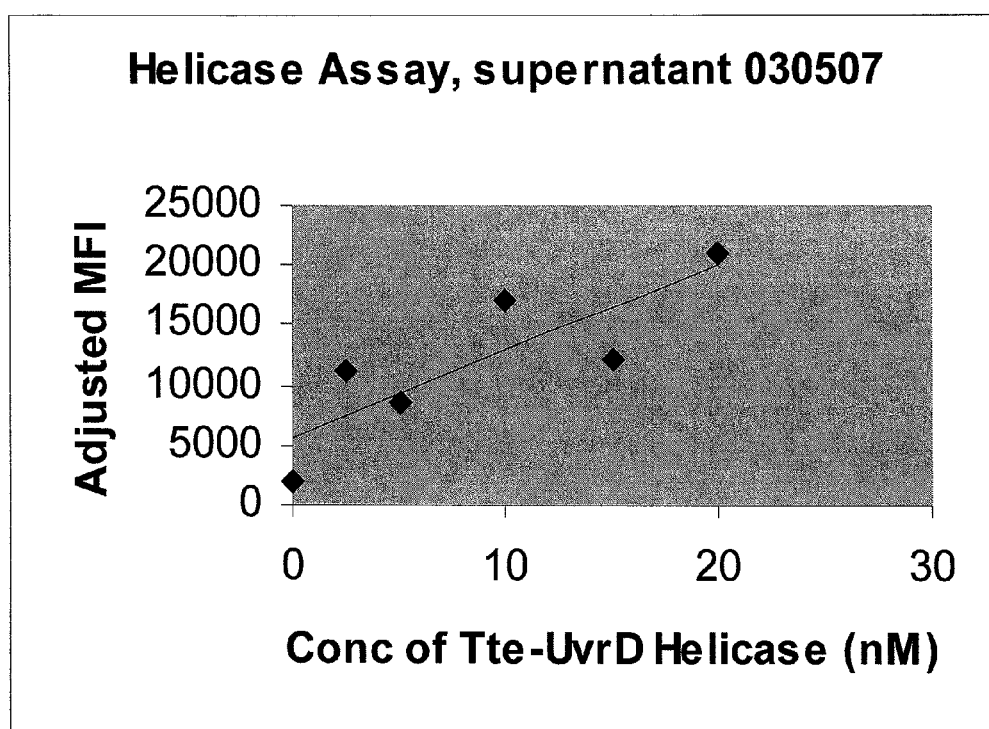
FIG. 6 depicts results from an experiment performance of the helicase assay at 55° C. On increasing helicase concentrations, there is an increase in fluorescence in the supernatant, representing release of the labeled strand from the immobilized duplex.

FIG. 5 is a plot of this data and represents the material bound to the plate (pellet). On increasing Helicase concentrations, there is a decrease in fluorescence units representing the loss of pHDAcy3 from pHDAbio and an increase in Helicase activity.

TABLE 7

Data depicting material released from the plate (supernatant).
Helicase AssaySupernatant
(030507NA)

| Material | Fluorescence | MFI | Std. Dev. | % CV | Corrected MFI | bkgd corrected MFI |
|---|---|---|---|---|---|---|
| 0 nM Helicase | 24472 19970 14825 | 19756 | 4827 | 24 | 16741 | 1879 |
| 2.5 nM Helicase | 30445 24113 32583 | 29047 | 4405 | 15 | 26032 | 11170 |
| 5 nM Helicase | 22657 24841 32064 | 26521 | 4923 | 19 | 23506 | 8644 |
| 10 nM Helicase | 33379 30961 40530 | 34957 | 4976 | 14 | 31942 | 17080 |
| 15 nM Helicase | 26244 35778 28185 | 30069 | 5038 | 17 | 27054 | 12192 |
| 20 nM Helicase | 25006 44095 47206 | 38769 | 12020 | 31 | 35754 | 20892 |
| 20 nM, NoATP | 14110 20438 16038 | 16862 | 3243 | 19 | 13847 | N/A |
| 20 nM, No pHDAC | 39672 22381 34813 | 32289 | 8918 | 28 | 29274 | 14412 |
| Oligo + Buffer | 19463 13632 8213 | 13769 | 5626 | 41 | 10754 | N/A |
| 0 nM, no pHDAC | 16310 17615 19705 | 17877 | 1713 | 10 | 14862 | 0 |
| No Oligo + buffer | 2419 1909 4716 | 3015 | 1495 | 50 | 0 | |
| 1/10 annealing mix | 14446 15597 14981 | 15008 | 576 | 4 | 11993 | |
| 1/100 annealing mix | 3120 3116 3352 | 3196 | 135 | 4 | 181 | |
| Unbound cy3 | 21680 19852 32454 | 24662 | 6810 | 28 | 21647 | |

FIG. 13 is a plot of the experimental results showing an increase in fluorescence units representing the release of pHDAcy3 in the supernatant and an increase in Helicase activity with increasing concentrations of Helicase. Performing the Helicase Assay at 55° C. did not show the increase in Helicase activity as has been previously reported. The range of enzyme concentration used may have been too low.

Example 4

Experiments were conducted to find the optimal temperature for Tte-UvrD Helicase Activity using the Helicase Assay. The assay was performed as outlined below in Example 6 with the exception that only two concentration points were used in the Helicase Assay, 10 nM and 20 nM and the temperatures ranged from 55° C. to 65° C. The different temperature points used were 55° C., 57° C., 60° C., 62° C., and 65° C.

Table 8 represents a compilation of four different tables representing the results from two different temperature points, 55° C. and 57° C.

TABLE 8A

Helicase Assay pellet 030607, 55 C.

| Material | RFU | MFI | Corrected MFI | Std. Dev. | % CV | S/N ratios |
|---|---|---|---|---|---|---|
| 0 nM Helicase | 21591 18887 18222 | 19567 | 18593 | 1784 | 9 | 1 |
| 10 nM Helicase | 13682 14051 13696 | 13810 | 12836 | 209 | 2 | 1.45 |
| 20 nM Helicase | 11741 12685 13753 | 12726 | 11752 | 1007 | 8 | 1.6 |
| 0 nM, no pHDAC | 18510 18470 17760 | 18247 | 17273 | 422 | 2 | N/A |
| 20 nM, NoATP | 18636 19172 20136 | 19315 | 18341 | 760 | 4 | N/A |
| Oligo + Buffer | 24487 19928 19867 | 21427 | 20453 | 2650 | 12 | N/A |
| No Oligo + buffer | 971 981 969 | 974 | 0 | 6 | 1 | N/A |

TABLE 8B

Helicase Assay pellet 030607, 57 C.

| Material | RFU | MFI | Corrected MFI | Std. Dev. | % CV | S/N ratios |
|---|---|---|---|---|---|---|
| 0 nM Helicase | 23872 20218 20073 | 21388 | 20206 | 2153 | 10 | 1 |
| 10 nM Helicase | 16395 16728 16349 | 16491 | 15309 | 207 | 1 | 1.32 |
| 20 nM Helicase | 13561 13710 13934 | 13735 | 12553 | 188 | 1 | 1.6 |
| Oligo + Buffer | 20842 21645 21318 | 21268 | 20086 | 404 | 2 | N/A |
| 20 nM, NoATP | 20550 20146 19776 | 20157 | 18975 | 387 | 2 | N/A |
| 0 nM, no pHDAC | 19292 20591 21194 | 20359 | 19177 | 972 | 5 | N/A |
| No Oligo + buffer | 1164 1197 1184 | 1182 | 0 | 17 | 1 | N/A |

TABLE 8C

Helicase Assay supernatant 030607, 55 C.

| Material | RFU | MFI | Corrected MFI | Std. Dev. | % CV | Corrected MFI | S/N ratios |
|---|---|---|---|---|---|---|---|
| 0 nM Helicase | 15278 14621 13746 | 14548 | 12007 | 769 | 5 | 4876 | 1 |
| 10 nM Helicase | 35861 30280 34911 | 33684 | 31143 | 2986 | 9 | 24012 | 4.9 |
| 20 nM Helicase | 21808 38744 41088 | 33880 | 31339 | 10520 | 31 | 24208 | 5 |
| 0 nM, no pHDAC | 5799 12977 10241 | 9672 | 7131 | 3623 | 37 | 0 | N/A |
| 20 nM, NoATP | 12312 14480 16329 | 14374 | 11833 | 2011 | 14 | 4702 | N/A |
| Oligo + Buffer | 15228 6033 4498 | 8586 | 6045 | 5803 | 68 | N/A | N/A |
| No Oligo + Buffer | 913 3265 3444 | 2541 | 0 | 1412 | 56 | N/A | N/A |

TABLE 8D

Helicase Assay supernatant 030607, 57 C.

| Material | RFU | MFI | Corrected MFI | Std. Dev. | % CV | Adjusted MFI | S/N ratios |
|---|---|---|---|---|---|---|---|
| 0 nM Helicase | 19455 15908 15087 | 16817 | 15647 | 2321 | 14 | 1791 | 1 |
| 10 nM Helicase | 24948 24177 23317 | 24147 | 22977 | 816 | 3 | 9121 | 5.1 |
| 20 nM Helicase | 39752 32242 30726 | 34240 | 33070 | 4833 | 14 | 19214 | 11 |
| Oligo + Buffer | 4835 12186 7393 | 8138 | 6968 | 3732 | 46 | N/A | N/A |
| 20 nM, NoATP | 10363 12982 9596 | 10980 | 9810 | 1775 | 16 | N/A | N/A |
| 0 nM, no pHDAC | 17445 12057 15576 | 15026 | 13856 | 2736 | 18 | 0 | N/A |
| No Oligo + buffer | 1195 1152 1163 | 1170 | 0 | 22 | 2 | N/A | N/A |

Table 9 represents a compilation of six different tables representing the results from three different temperature points, 60° C. and 62° C. and 65° C. Plotting all the S/N ratios that were obtained at different temperatures and two different concentrations of Tte-UvrD, the Helicase activities at different temperatures was compared.

TABLE 9A

Helicase Assay pellet 030607, 60 C.

| Material | RFU | MFI | Corrected MFI | Std. Dev. | % CV | S/N ratios |
|---|---|---|---|---|---|---|
| 0 nM Helicase | 10791 10726 10738 | 10752 | 9990 | 35 | 0 | 1 |
| 10 nM Helicase | 6584 6557 6650 | 6597 | 5835 | 48 | 1 | 1.7 |
| 20 nM Helicase | 4443 3913 4866 | 4407 | 3645 | 478 | 11 | 2.7 |
| Oligo + Buffer | 12063 12088 11617 | 11923 | 11161 | 265 | 2 | N/A |
| 20 nM, NoATP | 11360 11370 11441 | 11390 | 10628 | 44 | 0 | N/A |
| 0 nM, no pHDAC | 14957 11061 11473 | 12497 | 11735 | 2140 | 17 | N/A |
| No Oligo + buffer | 756 769 760 | 762 | 0 | 7 | 1 | N/A |

TABLE 9B

Helicase Assay pellet 030607, 62 C.

| Material | RFU | MFI | Corrected MFI | Std. Dev. | % CV | S/N ratios |
|---|---|---|---|---|---|---|
| 0 nM Helicase | 18000 18253 18888 | 18380 | 17162 | 457 | 2 | 1 |
| 10 nM Helicase | 9759 8180 8202 | 8714 | 7496 | 905 | 10 | 2.3 |
| 20 nM Helicase | 3512 3065 5462 | 4013 | 2795 | 1275 | 32 | 6.1 |
| Oligo + Buffer | 24001 23287 23148 | 23479 | 22261 | 458 | 2 | N/A |
| 20 nM, NoATP | 21586 21260 20896 | 21247 | 20029 | 345 | 2 | N/A |
| 0 nM, no pHDAC | 16938 19214 20147 | 18766 | 17548 | 1651 | 9 | N/A |
| No Oligo + buffer | 1197 1227 1230 | 1218 | 0 | 18 | 1 | N/A |

TABLE 9C

Helicase Assay pellet 030607, 65 C.

| Material | RFU | MFI | Corrected MFI | Std. Dev. | % CV | S/N ratios |
|---|---|---|---|---|---|---|
| 0 nM Helicase | 6113 6039 6425 | 6192 | 5677 | 205 | 3 | 1 |
| 10 nM Helicase | 1431 1684 1661 | 1592 | 1077 | 140 | 9 | 5.3 |
| 20 nM Helicase | 874 861 686 | 807 | 292 | 105 | 13 | 19.4 |
| Oligo + Buffer | 8601 8733 9678 | 9004 | 8489 | 587 | 7 | N/A |
| 20 nM, NoATP | 8674 7458 7127 | 7753 | 7238 | 815 | 11 | N/A |
| 0 nM, no pHDAC | 4898 5922 5111 | 5310 | 4795 | 540 | 10 | N/A |
| No Oligo + buffer | 509 521 516 | 515 | 0 | 6 | 1 | N/A |

TABLE 9D

Helicase Assay supernatant 030607, 60 C.

| Material | RFU | MFI | Corrected MFI | Std. Dev. | % CV | Adjusted MFI | S/N ratios |
|---|---|---|---|---|---|---|---|
| 0 nM Helicase | 16332 16791 12741 | 15288 | 14473 | 2218 | 15 | 1075 | 1 |
| 10 nM Helicase | 25807 30620 33686 | 30038 | 29223 | 3972 | 13 | 15825 | 14.7 |
| 20 nM Helicase | 39851 45462 42344 | 42552 | 41737 | 2811 | 7 | 28339 | 26.4 |
| Oligo + Buffer | 9874 9851 9860 | 9862 | 9047 | 12 | 0 | N/A | N/A |
| 20 nM, NoATP | 11233 10222 13454 | 11636 | 10821 | 1653 | 14 | N/A | N/A |
| 0 nM, no pHDAC | 12895 15603 14142 | 14213 | 13398 | 1355 | 10 | 0 | N/A |
| No Oligo + buffer | 830 895 721 | 815 | 0 | 88 | 11 | N/A | N/A |

TABLE 9E

Helicase Assay supernatant 030607, 62 C.

| Material | RFU | MFI | Corrected MFI | Std. Dev. | % CV | Adjusted MFI | S/N ratios |
|---|---|---|---|---|---|---|---|
| 0 nM Helicase | 33218 28456 29642 | 30439 | 29051 | 2479 | 8 | 3616 | 1 |
| 10 nM Helicase | 41752 40831 42619 | 41734 | 40346 | 894 | 2 | 14911 | 4.1 |
| 20 nM Helicase | 44277 49167 48025 | 47156 | 45768 | 2558 | 5 | 20333 | 5.6 |
| Oligo + Buffer | 20326 33674 30632 | 28211 | 26823 | 6996 | 25 | 1388 | N/A |

TABLE 9E-continued

Helicase Assay supernatant 030607, 62 C.

| Material | RFU | MFI | Corrected MFI | Std. Dev. | % CV | Adjusted MFI | S/N ratios |
|---|---|---|---|---|---|---|---|
| 20 nM, NoATP | 9503<br>10216<br>15709 | 11809 | 10421 | 3396 | 29 | N/A | N/A |
| 0 nM, no pHDAC | 27169<br>35484<br>33510 | 32054 | 30666 | 4344 | 14 | 5231 | N/A |
| No Oligo + buffer | 1372<br>1363<br>1430 | 1388 | 0 | 36 | 3 | N/A | N/A |

TABLE 9F

Helicase Assay supernatant 030607, 65 C.

| Materials | RFU | MFI | Corrected MFI | Std. Dev. | % CV | Adjusted MFI | S/N ratios |
|---|---|---|---|---|---|---|---|
| 0 nM Helicase | 17798<br>7380<br>15955 | 13711 | 13169 | 5560 | 41 | 4514 | 1 |
| 10 nM Helicase | 26027<br>38690<br>33971 | 32896 | 32354 | 6400 | 19 | 23699 | 5.25 |
| 20 nM Helicase | 34835<br>32652<br>43237 | 36908 | 36366 | 5589 | 15 | 27711 | 6.14 |
| Oligo + Buffer | 10170<br>8778<br>5844 | 8264 | 7722 | 2208 | 27 | N/A | N/A |
| 20 nM, NoATP | 11397<br>8759<br>10408 | 10188 | 9646 | 1333 | 13 | 991 | N/A |
| 0 nM, no pHDAC | 19951<br>6073<br>1567 | 9197 | 8655 | 9582 | 104 | 0 | N/A |
| No Oligo + buffer | 484<br>535<br>608 | 542 | 0 | 62 | 11 | N/A | N/A |

Figure 7:
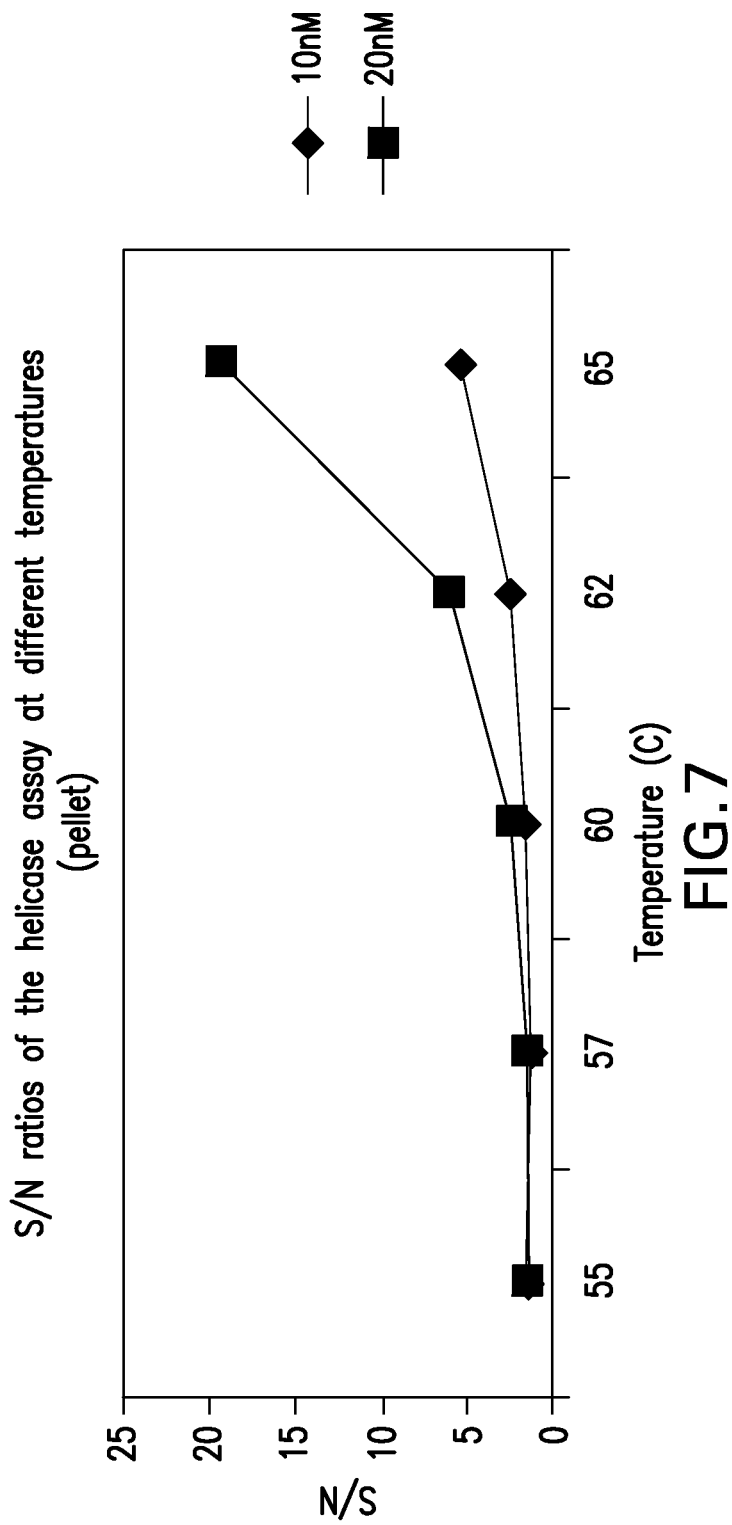
FIG. 7 shows experimental results comparing helicase activities at different temperatures using the signal: noise (S/N) ratios obtained from the pellet fraction. The greatest signal to noise ratio occurred at 65° C.
Figure 8:
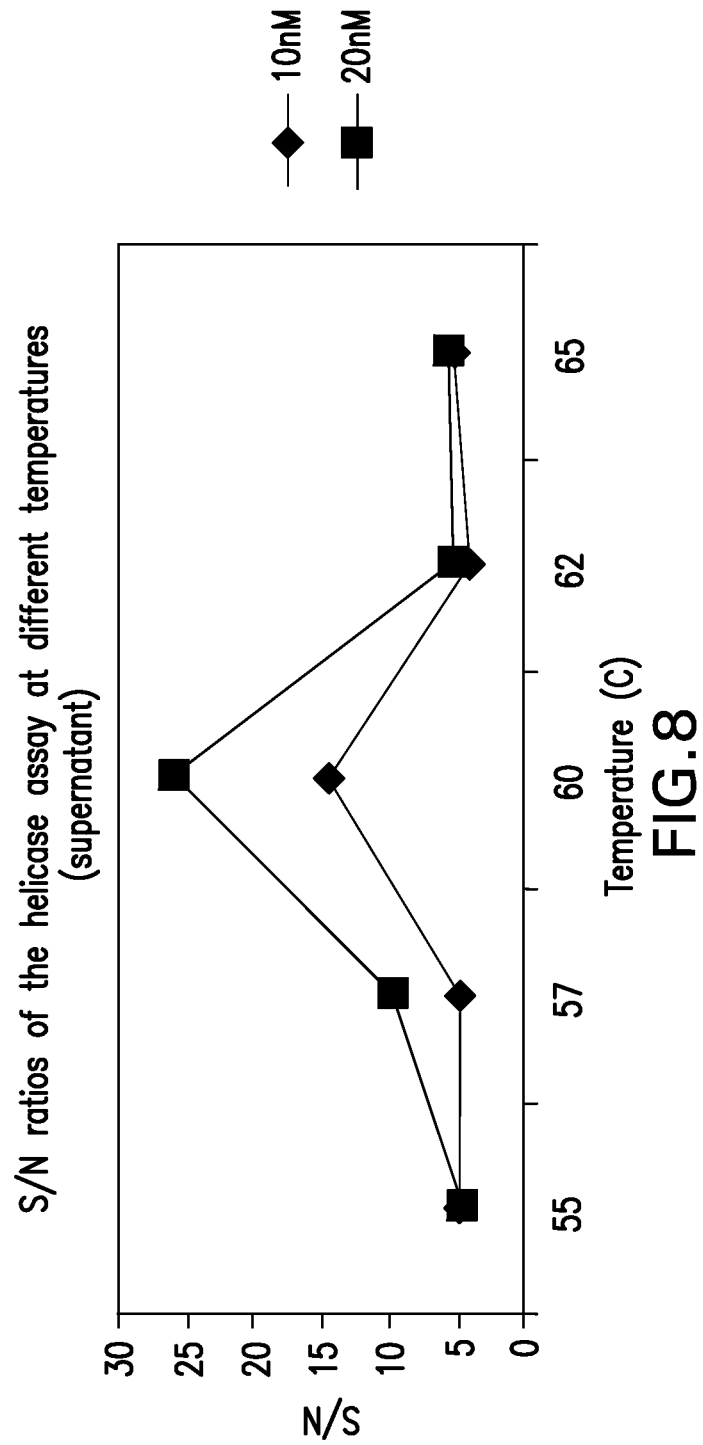
FIG. 8 shows experimental results comparing helicase activities at different temperatures using the signal: noise (S/N) ratios obtained from the supernatant fraction. The greatest signal to noise ratio occurred at 60° C.

FIG. 7 depicts a comparison of the Tte-UvrD Helicase activities at different temperatures using the S/N values obtained from the pellet. FIG. 8 depicts a comparison of the Tte-UvrD Helicase activities at different temperatures using the S/N values obtained from the supernatant. Looking at the values obtained for the pellet, the temperature point that shows the greatest signal to noise ratio is 65° C.; however looking at the results from the supernatant, the greatest signal to noise ratio is 60° C.

Example 5

In this experiment, a direct comparison between ATP and dATP in the Helicase Assay was performed. The Assay was again carried out as in Example 4 but in some instances 3 mM dATP was added instead of 3 mM ATP and half the supernatant was added to the streptavidin coated plate instead of the entire mix.

Table 10 depicts data obtained from analyzing the pellet fraction and performing a comparison of ATP vs. dATP (in BOLD).

Table 11 (A) and (B) give a side by side comparison of the different values obtained in the Helicase Assay using ATP vs. dATP. Looking at both plots, the results for ATP and dATP were very comparable and there were minimal differences seen between the two. The Table depicts data obtained from analyzing the supernatant fraction and performing a comparison of ATP vs. dATP (in BOLD).

Helicase Assay 030907, 60 C. ATP, vs dATP (red)

| Material | RFU | MFI | Corrected MFI | Std. Dev. | % CV |
|---|---|---|---|---|---|
| 0 nM Helicase | 3621<br>4415<br>4648 | 4228 | 4019 | 538 | 13 |
| 2.5 nM Helicase | 4195<br>4363<br>3955 | 4171 | 3962 | 205 | 5 |
| 5 nM Helicase | 3384<br>3390<br>3446 | 3407 | 3198 | 34 | 1 |
| 10 nM Helicase | 2943<br>3042<br>3097 | 3027 | 2818 | 78 | 3 |
| 15 nM Helicase | 2361<br>2422<br>2322 | 2368 | 2159 | 50 | 2 |
| 20 nM Helicase | 1102<br>1788<br>1811 | 1567 | 1358 | 403 | 26 |
| 20 nM, NoATP | 4858<br>4849<br>3518 | 4408 | 4199 | 771 | 17 |
| 0 nM, No pHDAC | 4716<br>4440<br>4301 | 4486 | 4277 | 211 | 5 |
| Oligo + Buffer | 4846<br>4918<br>5096 | 4953 | 4744 | 129 | 3 |
| No Oligo + buffer | 212<br>206<br>208 | 209 | 0 | 3 | 1 |
| 2.5 nM Helicase | 3889<br>4096<br>3864 | 3950 | 3741 | 127 | 3 |
| 5 nM Helicase | 3231<br>2340<br>3470 | 3014 | 2805 | 596 | 20 |
| 10 nM Helicase | 2805<br>2626<br>2733 | 2721 | 2512 | 90 | 3 |
| 15 nM Helicase | 2497<br>2672<br>2420 | 2530 | 2321 | 129 | 5 |
| 20 nM Helicase | 1009<br>1648<br>2047 | 1568 | 1359 | 524 | 33 |

Helicase Assay 030907, 60 C. ATP vs dATP(bold), supernatant

| Material | RFU | MFI | Corrected MFI | Std. Dev | % CV | Adjusted MFI |
|---|---|---|---|---|---|---|
| 0 nM Helicase | 405<br>462<br>491 | 453 | 354 | 44 | 10 | 156 |
| 2.5 nM Helicase | 552<br>664<br>453 | 556 | 457 | 106 | 19 | 259 |
| 5 nM Helicase | 431<br>447<br>333 | 404 | 305 | 62 | 15 | 107 |

-continued

Helicase Assay 030907, 60 C. ATP vs dATP(bold), supernatant

| Material | RFU | MFI | Corrected MFI | Std. Dev | % CV | Adjusted MFI |
|---|---|---|---|---|---|---|
| 10 nM Helicase | 1158 958 417 | 844 | 745 | 383 | 45 | 547 |
| 15 nM Helicase | 1397 1699 1301 | 1466 | 1367 | 208 | 14 | 1169 |
| 20 nM Helicase | 455 526 1690 | 890 | 791 | 693 | 78 | 593 |
| 20 nM, No ATP | 232 288 345 | 288 | 189 | 57 | 20 | N/A |
| 0 nM, No pHDAC | 355 284 251 | 297 | 198 | 53 | 18 | 0 |
| Oligo + Buffer | 209 253 274 | 245 | 146 | 33 | 14 | N/A |
| No Oligo + buffer | 101 96 101 | 99 | 0 | 3 | 3 | N/A |
| 2.5 nM Helicase | 406 840 744 | 663 | 564 | 228 | 34 | 366 |
| 5 nM Helicase | 1060 743 706 | 836 | 737 | 195 | 23 | 539 |
| 10 nM Helicase | 813 1143 468 | 808 | 709 | 338 | 42 | 511 |
| 15 nM Helicase | 630 627 699 | 652 | 553 | 41 | 6 | 355 |
| 20 nM Helicase | 651 601 656 | 636 | 537 | 30 | 5 | 339 |

The table represents the plot of the supernatants from the Helicase assay using ATP vs. dATP, respectively. A direct comparison of using ATP or dATP in the Helicase assay (pellet) shows that the two compounds are very comparable. Looking at the supernatant, the results were very variable and this does not seem to be a very efficient way at looking at the Helicase activity. The variation in the results seen for the supernatant could stem from the fact that the samples were being transferred twice, once to a regular 96-well plate and then again to the streptavidin coated plate. This could have resulted in loss of samples during transfer. Additionally, the supernatant consists of a mix of different added reagents (e.g. Helicase ATP, trap oligo), and some of the constituents from these reagents may lead to the variability seen. Because of the increased variability seen using the supernatant, the pellet values were used when assessing the Helicase assay.

Example 6

Since dATP/ATP is usually added after the reaction mixture has been at the desired temperature for two minutes, the effect on the Helicase Assay was tested of premixing dATP in the reaction mix and allowing the reaction to proceed at 65° C.
Annealing of Duplex Oligos:
1) Dissolve each of the labeled complementary oligo in ThermoPol Buffer (20 mM, Tris-HCl, pH 8.8, 10 mM KCl, 10 mM $(NH_4)_2SO_4$, 2 mM $MgSO_4$, 0.1% Triton-X100).
2) Combine 75 nM of pHDAbio dissolved oligo with 50 nM of pHDAcy3 dissolved oligo in a 1.5 mL microfuge tube and incubate at 95° C. for 2 min on a heating block. Remove the tube from the heating block and cool down to room temperature by placing tube in rack on bench (approximately 70-90 min). Place the tube in ice until further use. The reaction volume for each annealing reaction was 30 ul.

Attaching Annealed Mix to Streptavidin Coated Plate
3) Prewash the streptavidin coated plates with 200 ul wash buffer (25 mM Tris-HCl, pH 7.4, 0.05% Tween-20, 150 mM NaCl).
4) Add 30 ul of wash buffer to each 30 ul of annealing mix. Add the entire mix (60 ul total) to each well of the streptavidin coated plate.
5) Incubate the plate at RT for 30 min with shaking.

Addition of Helicase Mix
6) Remove the liquid and wash the well three times with wash buffer. Add different concentrations of Tte-UvrD Helicase and capture oligo (pHDAC) at a concentration of 400 nM in a total reaction volume of 50 ul in ThermoPol Buffer (20 mM, Tris-HCl, pH 8.8, 10 mM KCl, 10 mM $(NH_4)_2SO_4$, 2 mM $MgSO_4$, 0.1% Triton-X100). Pre-incubate at 65° C. for 2 min
7) Initiate the reaction by adding dATP to 3 mM and continue incubation at 65° C. for 10 min
8) Remove the liquid and wash the streptavidin coated plate containing bound material (pellet) three times with streptavidin wash buffer. Add 50 ul water to each well.
9) Incubate the plate with the pellet at RT for 60 min with shaking.
10) Read the plates in a fluorescent plate reader with excitation of 535 nm and emission of 590 nm.

Alternatively after step 5:
Addition of Helicase Mix
6) Remove the liquid and wash the well three times with wash buffer. Add different concentrations of Tte-UvrD Helicase, capture oligo (pHDAC) at a concentration of 400 nM and dATP at a concentration of 3 mM in a total reaction volume of 50 ul in ThermoPol Buffer (20 mM, Tris-HCl, pH 8.8, 10 mM KCl, 10 mM $(NH_4)_2SO_4$, 2 mM $MgSO_4$, 0.1% Triton-X100).
7) Incubate the plate at 65° C. for 10 min
8) Remove the liquid and wash the streptavidin coated plate containing bound material (pellet) three times with streptavidin wash buffer. Add 50 ul water to each well.
9) Incubate the plate with the pellet at RT for 60 min with shaking.
10) Read the plates in a fluorescent plate reader with excitation of 535 nm and emission of 590 nm.

The capture oligo concentration used in this experiment was 400 nM instead of 800 nM, and the concentration of Helicase used ranged between 1.25 to 10 nM. The different concentration points used were 1.25 nM, 2.5 nM, 5 nM, 7.5 nM and 10 nM. In order to aid in the addition of Helicase to the reaction mix, a freshly made diluted stock of Helicase (25 ng/ul) was made in ThermoPol Buffer from the original 150 ng/ul stock of Tte-UvrD Helicase.

Table 12 provides a table of data obtained using original method of dATP addition, where dATP is added individually to each well. FIG. 11 (A) depicts the plot showing all the data points from the assay ranging from 0 nM to 10 nM and from the graph, one can see that the linear range of this assay starts breaking down around 7.5 nM at 65° C. FIG. 11 (B) depicts the plot showing the first four data points where the linear range is still in tact.

Helicase Assay 031607, 65 C., original, pellet

| Material | RFU | MFI | Corrected MFI | Std. Dev. | % CV |
|---|---|---|---|---|---|
| 0 nM Helicase | 32614 34041 35461 | 34039 | 31284 | 1424 | 4 |
| 1.25 nM Helicase | 25646 23626 25869 | 25047 | 22292 | 1236 | 5 |
| 2.5 nM Helicase | 21519 21378 24243 | 22380 | 19625 | 1615 | 7 |
| 5 nM Helicase | 14196 13717 15303 | 14405 | 11650 | 813 | 6 |
| 7.5 nM Helicase | 13628 13687 13943 | 13753 | 10998 | 167 | 1 |
| 10 nM Helicase | 8480 9102 8217 | 8600 | 5845 | 454 | 5 |
| 0 nM, no pHDAC | 38529 39944 35565 | 38013 | 35258 | 2235 | 6 |
| 10 nM, NoATP | 43419 44153 42421 | 43331 | 40576 | 869 | 2 |
| Oligo + Buffer | 45742 45889 44274 | 45302 | 42547 | 893 | 2 |
| No Oligo + buffer | 2773 2714 2779 | 2755 | 0 | 36 | 1 |

Figure 12:
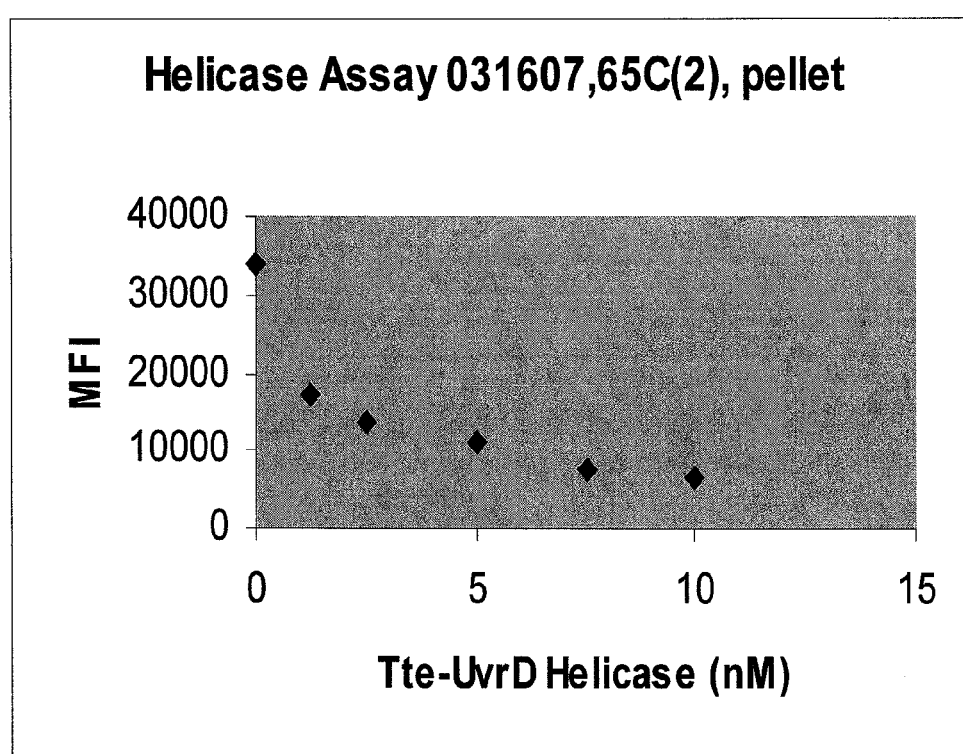
FIG. 12 depicts the plot showing all the data points from the helicase assay conducted with a range of helicase concentrations and in which dATP is pre-mixed in the reaction mix. The linear range falls off quickly and proves that this would not be an effective way to add dATP to the helicase assay.

Table 13 provides a table of data obtained from premixing dATP to the reaction mixture. FIG. 12 presents the plot of this data showing data points obtained from pre-mixing dATP in the reaction mix. Note that the linear range of the graph breaks down almost instantaneously. The helicase reaction is allowed to proceed immediately, and so this would not be an effective way to add dATP to the Helicase Assay.

Helicase Assay 031607, 65 C., alternate, pellet

| Material | RFU | MFI | Corrected MFI | Std. Dev. | % CV |
|---|---|---|---|---|---|
| 0 nM Helicase | 35839 37531 38870 | 37413 | 34155 | 1519 | 4 |
| 1.25 nM Helicase | 26527 17385 17697 | 20536 | 17278 | 5190 | 25 |
| 2.5 nM Helicase | 13064 18477 19345 | 16962 | 13704 | 3404 | 20 |
| 5 nM Helicase | 13213 14517 14824 | 14185 | 10927 | 855 | 6 |
| 7.5 nM Helicase | 11877 10488 9912 | 10759 | 7501 | 1010 | 9 |
| 10 nM Helicase | 9146 10377 10361 | 9961 | 6703 | 706 | 7 |
| 0 nM, no pHDAC | 37313 34492 32254 | 34686 | 31428 | 2535 | 7 |
| 10 nM, NoATP | 42416 41845 40782 | 41681 | 38423 | 829 | 2 |
| Oligo + Buffer | 45346 47001 46679 | 46342 | 43084 | 877 | 2 |
| No Oligo + buffer | 3296 3228 3251 | 3258 | 0 | 35 | 1 |

Comparison of adding the dATP individually after the reaction has been pre-heated to 65° C. vs. adding the dATP in the reaction mix from the beginning shows that using pre-mixed dATP is not an efficient way to add dATP to the Helicase assay as the linear range breaks down instantly.

Example 7

The following experiment was conducted to apply the Helicase Assay to assign Unit Definition for Tte-UvrD Helicase. The purity of BioHelix Tte-UvrD was assessed to be about 95% pure (information obtained from BioHelix using gel analysis of the purified protein).

TABLE 14

| Material | RFU | MFI | Corrected MFI | Std. Dev | % CV | Conc of pHHDAcy3 |
|---|---|---|---|---|---|---|
| 1/100 annealing mix | 5101 5159 5192 | 5151 | 2370 | 46 | 1 | 0.025 pmoles |
| Buffer | 2744 2817 2780 | 2780 | 0 | 37 | 1 | N/A |

Table 14 summarizes data obtained from the experiment. The annealing Mix from Step 1 in the Helicase Assay, containing a known amount of pHDAcy3 was diluted 100 fold in water. 50 ul of this mix was added directly to a well in the streptavidin coated plate and read on the fluorescent plate reader. To convert from nM to moles a conversion tool from was used; use the MW of Tte-UvrD Helicase as 82.66 kDa.

Using the values above, at 0 nM Helicase, a reading of 31284 would correspond to approximately 0.33 pmoles of pHDACy3 bound.

Using the Unit definition of Tte-UvrD Helicase as: The release of 0.1 pmoles of Cy3 labeled oligonucleotide from its complementary strand for 10 min at 65° C., then 0.1 pmoles of pHDAcy3 would be equivalent to 9480 MFI, the release of 0.1 pmoles would be equivalent to 31284−9480=21804 MFI.

Using the equation above, a value of 2.03 nM of Helicase was obtained from the data shown in Table 7.

Using the value of 2.03 nM of Helicase, this would be equivalent to 0.182 ng/ul; since the reaction volume used was 50 ul, this would then result in 8.4 ng of Tte-UvrD Helicase. Specific activity of Tte-UvrD Helicase would be 1 U/8.4 ng which would be equivalent to 119000 U/mg, thus the specific activity of Tte-UvrD Helicase at 65° C. is 119000 U/mg.

Using similar methods of calculations at 55° C. and 60° C., specific activities of Tte-UvrD Helicase were also obtained. The specific activity of Tte-UvrD Helicase at 55° C. is 13,750 U/mg. The specific activity of Tte-UvrD at 60° C. was calculated under two conditions, using ATP and using dATP. The specific activity of Tte-UvrD Helicase using ATP was 27,500

U/mg, while the specific activity of Tte-UvrD Helicase using dATP was 31,000 U/mg. This indicates that ATP and dATP were comparable for use in the Helicase assay with dATP giving slightly better results in the Helicase activity.

The greatest specific activity was seen using Tte-UvrD at 65° C. suggesting that this is the optimal temperature for helicase activity.

What is claimed is:

1. A method for measuring helicase activity comprising:
   a. providing a nucleic acid duplex comprising a first immobilizable nucleic acid strand and a labeled second strand;
   b. immobilizing the nucleic acid duplex;
   c. contacting the immobilized nucleic acid substrate duplex with a helicase to form a helicase-duplex mixture;
   d. incubating the helicase-duplex mixture with a trap oligonucleotide under conditions for helicase activity, wherein the trap oligonucleotide binds to the labeled second strand;
   e. separating non-immobilized nucleic acids, wherein the non-immobilized nucleic acids comprise the trap oligonucleotide bound to labeled second strand; and
   f. detecting the label present with the immobilized nucleic acids, wherein a decrease in the amount of label present indicates helicase activity.

2. The method of claim 1, further comprising detecting the amount of label present after step a) or step b).

3. The method of claim 2, further comprising comparing the amount of label present in step a) or b) with the amount of label present in step f).

4. The method of claim 1, wherein in step d), a duplex can form between the trap oligonucleotide and the labeled second strand.

5. The method of claim 1, further comprising quantifying the amount of helicase activity by comparing the amount of label present after step a) or b) to the amount of label present in step f).

6. The method of claim 1, wherein the helicase is Tte-UvrD helicase.

7. The method of claim 1, wherein the trap oligonucleotide is complementary to the labeled second strand, and they hybridize to each other.

8. The method of claim 1, wherein the trap oligonucleotide is present in excess.

9. The method of claim 1, wherein ATP, dATP, UTP, CTP, dCTP, GTP or dTTP is added during step c).

10. The method of claim 1, wherein steps (a), (b), (c), and/or (d) are carried out simultaneously.

11. A method for measuring helicase activity comprising:
   a. providing a nucleic acid duplex comprising a first immobilizable nucleic acid strand and a labeled second strand;
   b. immobilizing the nucleic acid duplex;
   c. contacting the immobilized nucleic acid substrate duplex with a helicase to form a helicase-duplex mixture;
   d. incubating the helicase-duplex mixture with a trap oligonucleotide under conditions for helicase activity, wherein the trap oligonucleotide binds to the labeled second strand;

e. separating non-immobilized nucleic acids, wherein the non-immobilized nucleic acids comprise the trap oligonucleotide bound to labeled second strand; and f. detecting the amount of label present with the non-immobilized nucleic acids, wherein the presence of label over background indicates helicase activity.

12. The method of claim 11, wherein an immobilizable trap oligonucleotide-labeled second strand duplex forms in step c).

13. A method for measuring helicase activity comprising:
a. providing a nucleic acid duplex comprising a first immobilizable nucleic acid strand and a labeled second strand;
b. determining the amount of label present;
c. immobilizing the nucleic acid duplex;
d. contacting the immobilized nucleic acid substrate duplex with a helicase to form a helicase-duplex mixture;
e. incubating the helicase-duplex mixture with a trap oligonucleotide comprising a quencher under conditions for helicase activity; and
f. detecting the label present with the immobilized nucleic acids, wherein a decrease in the amount of label present indicates helicase activity.

14. The method of claim 13, wherein steps (a) through (f) are conducted in a homogenous assay.

15. The method of claim 1, wherein the temperature during step (d) is higher than room temperature.

16. The method of claim 1, wherein detecting the label is performed using direct fluorescence.

17. The method of claim 13, wherein the labeled second is a modified Taqman probe.

* * * * *